US008691768B2

(12) United States Patent
Fields et al.

(10) Patent No.: US 8,691,768 B2
(45) Date of Patent: Apr. 8, 2014

(54) METHODS OF DETERMINING DELTA OPIOID RECEPTOR SUBTYPES

(75) Inventors: Howard L. Fields, Berkeley, CA (US); Jennifer M. Mitchell, Berkeley, CA (US); Elyssa B. Margolis, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 12/990,487

(22) PCT Filed: May 1, 2009

(86) PCT No.: PCT/US2009/042634
§ 371 (c)(1),
(2), (4) Date: Oct. 29, 2010

(87) PCT Pub. No.: WO2010/036401
PCT Pub. Date: Apr. 1, 2010

(65) Prior Publication Data
US 2011/0046064 A1 Feb. 24, 2011

Related U.S. Application Data

(60) Provisional application No. 61/049,731, filed on May 1, 2008.

(51) Int. Cl.
*A61K 38/00* (2006.01)
*A61P 25/04* (2006.01)

(52) U.S. Cl.
USPC ........................................ 514/17.7; 514/18.4

(58) Field of Classification Search
None
See application file for complete search history.

(56) References Cited

U.S. PATENT DOCUMENTS

| 5,352,680 | A | 10/1994 | Portoghese et al. |
| 5,411,965 | A | 5/1995 | Reid et al. |
| 5,780,479 | A | 7/1998 | Kim |
| 6,071,918 | A | 6/2000 | Cook |
| 6,103,722 | A | 8/2000 | Schultz et al. |
| 7,172,767 | B2 | 2/2007 | Kaiko et al. |
| 2006/0069086 | A1 | 3/2006 | Michalow et al. |
| 2006/0104907 | A1 | 5/2006 | Lazarus et al. |
| 2006/0178307 | A1 | 8/2006 | Bartlett et al. |
| 2007/0099947 | A1 | 5/2007 | Dean, III et al. |
| 2009/0214650 | A1 | 8/2009 | Ehrich |

FOREIGN PATENT DOCUMENTS

| WO | WO 94/06426 | 3/1994 |
| WO | WO 2007/041544 A1 | 4/2007 |

OTHER PUBLICATIONS

European Patent Office, Supplementary European Search Report, European Patent Application No. 09816621.8, Oct. 31, 2011, five pages.
Acosta, C. et al., "δ Opioid Receptor Modulation of Several Voltage-Dependent Ca2+ Currents in Rat Sensory Neurons," *The Journal of Neuroscience*, Oct. 1999, pp. 8337-8348, vol. 19, No. 19.
Aronin, N. et al., "Ultrastructural Localization and Biochemical Features of Immunoreactive Leu-enkephalin in Monkey Dorsal Horn," *The Journal of Neuroscience*, Jun. 1981, pp. 561-577, vol. 1, No. 6.
Chan, K. et al., "The Effect of the Irreversible μ-opioid Receptor Antagonist Clocinnamox on Morphine Potency, Receptor Binding and Receptor in mRNA," *European Journal of Pharmacology*, 1995, pp. 135-143, vol. 287.
Dickenson, A. et al., "Opioid Receptor Subtypes in the Rat Spinal Cord: Electrophysiological Studies with μ- and δ-opioid Receptor Agonists in the Control of Nociception," *Brain Research*, 1987, pp. 36-44, vol. 413, No. 1.
Gulya, K. et al., "Central Effects of the Potent and Highly Selective μ-Opioid Antagonist D-Phe-Cys-Tyr-D-Trp-Orn-Thr-Pen-Thr-$NH_2$ (CTOP) in Mice," *European Journal of Pharmacology*, 1988, pp. 355-360, vol. 150.
Hayes, A.G. et al., "Effect of β-funaltrexamine on Opioid Side-effects Produced by Morphine and U-50, 488H," *Journal of Pharmacy and Pharmacology*, 1985, pp. 841-843, vol. 37.
June, H.L. et al., "The $δ_2$-Opioid Receptor Antagonist Naltriben Reduces Motivated Responding for Ethanol," *Psychopharmacology (Berl)*, 1999, pp. 81-89, vol. 147, No. 1.
Kamei et al., "Streptozotocin-induced Diabetes Selectively Reduces Antinociception Mediated by $μ_1$-opioid Receptors, but Not That Mediated by $μ_2$-opioid Receptors," *Neuroscience Letters*, 1994, pp. 141-143, vol. 165, No. 1-2.
Kamei, J. et al., "Antinociceptive Effects of the Selective Non-peptidic δ-opioid Receptor Agonist TAN-67 in Diabetic Mice," *European Journal of Pharmacology.*, 1995, pp. 131-135, vol. 276.
Knapp et al., "Properties of TAN-67, a Nonpeptidic δ-opioid Receptor Agonist, at Cloned Human δ- and μ-opioid Receptors," *European Journal of Pharmacology*, 1995, pp. 129-234, vol. 291.
Krishnan-Sarin, et al., "The $Delta_2$-Opioid Receptor Antagonist Naltriben Selectively Attenuates Alcohol Intake in Rats Bred for Alcohol Preference," *Pharmacology Biochemistry Behavior*, 1995, pp. 153-159, vol. 52, No. 1.

(Continued)

*Primary Examiner* — Gregory S Emch
*Assistant Examiner* — Adam M Weidner
(74) *Attorney, Agent, or Firm* — Fenwick & West LLP

(57) ABSTRACT

The present invention provides methods of treating or preventing a substance-related disorder using selective delta opioid receptor-1 (DOP-R1) agonists, delta opioid receptor-2 (DOP-R2) antagonists, and/or mu opioid receptor (MOP-R) antagonists, or a pharmaceutically acceptable salt, solvate, hydrate, or prodrug thereof. The methods provided herein further comprise administering a therapeutically effective amount of a combination of a DOP-R1 agonist and a DOP-R2 antagonist. The methods also comprise administering a therapeutically effective amount of a combination of a DOP-R1 agonist and an MOP-R antagonist. The methods provided herein further comprise administering a therapeutically effective amount of a combination of a DOP-R1 agonist and a DOP-R2 antagonist and a MOP-R antagonist. The invention also relates to compositions containing the same. The invention also relates to methods of determining delta opioid receptor specificity of candidate agents.

2 Claims, 13 Drawing Sheets

(56) References Cited

OTHER PUBLICATIONS

Figure 1:
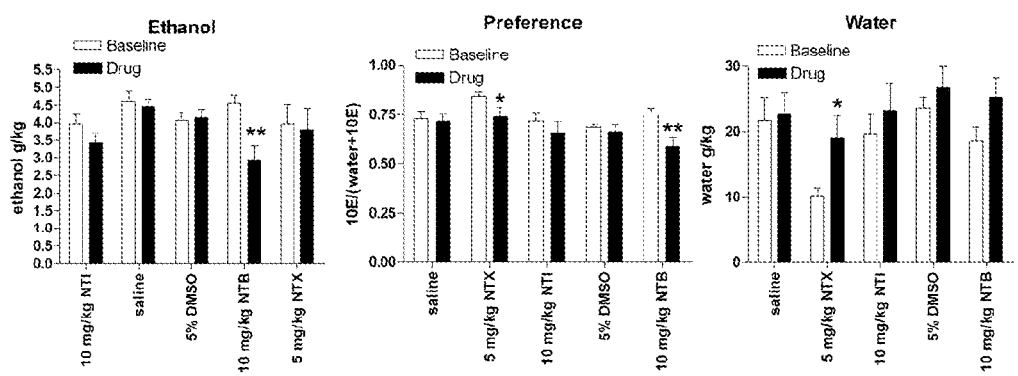
Figure 1:
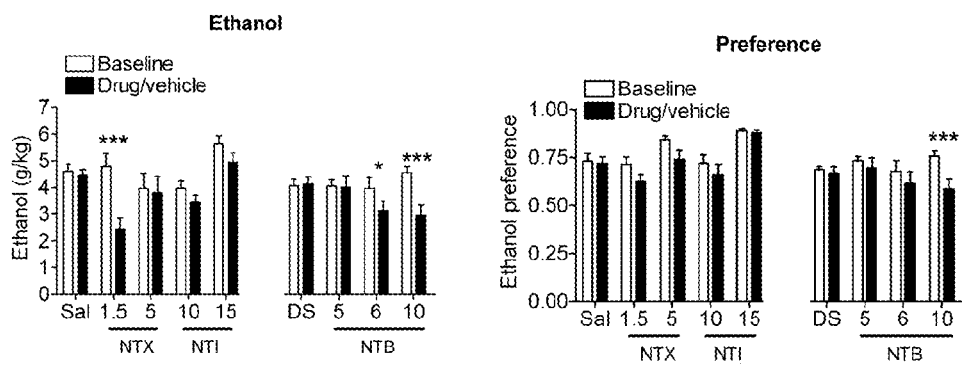

Levine, J.D. et al., "Peptides and the Primary Afferent Nociceptor," *The Journal of Neuroscience*, 1993, pp. 2273-2286, vol. 13, No. 6.

Miller, K.E. et al., "Comparison of Met-Enkephalin, Dynorphin A, and Neurotensin Immunoreactive Neurons in the Cat and Rat Spinal Cords. II. Segmental Differences in the Marginal Zone," *The Journal of Comparative Neurology*, 1989, pp. 619-628, vol. 279.

Miyamoto, Y. et al., "Involvement of $Delta_2$ Opioid Receptors in the Development of Morphine Dependence in Mice," *Journal of Pharmacology and Experimental Therapeautics*, 1993, pp. 1141-1145, vol. 264, No. 3.

Miyamoto, Y. et al., "Involvement of $Delta_2$ Opioid Receptors in Acute Dependence on Morphine in Mice," *Journal of Pharmacology and Experimental Therapeutics*, 1993, pp. 1325-1327, vol. 265, No. 3.

Narita, M. et al., "Stimulation of Spinal δ-opioid Receptors in Mice Selectively Enhances the Attenuation of δ-opioid Receptor-mediated Antinociception by Antisense Oligodeoxynucleotide," *European Journal of Pharmacology*, 1995, pp. 185-189, vol. 284, Issues 1-2.

Pasternak, G.W., "Insights into Mu Opioid Pharmacology: The Role of Mu Opioid Receptor Subtypes," *Life Sciences*, 2001, pp. 2213-2219, vol. 68.

Ramabadran, K. et al., "The Role of Endogenous Opioid Peptides in the Regulation of Pain," *Critical Reviews in Neurobiology*, 1990, pp. 13-32, vol. 6, Issue 1.

Rios, G.R. et al., "Inhibition and Active Sites of UDP-glucuronosyltransferases 2B7 and 1A1," *Drug Metabolism Disposition*, 2002, pp. 1364-1367, vol. 30, No. 12.

Schmidhammer, H. et al., "Synthesis and Biological Evaluation of 14-Alkoxymorphinans," *J. Med. Chem*, 1989, pp. 418-421, vol. 32.

Standifer, K. et al., "Selective Loss of Delta Opioid Analgesia and Binding by Antisense Oligodeoxynucleotides to a Delta Opioid Receptor," *Neuron*, 1994, pp. 805-810, vol. 12, No. 4.

Stewart, P.E. et al., "Evidence for Delta Opioid Receptor Substypes in Rat Spinal Cord: Studies with Intrathecal Naltriben, Cyclic[D-Pen$^2$, D-Pen$^5$] Enkephalin and [D-Ala$^2$, Glu$^4$] Deltorphin," *Journal of Pharmacology and Experimental Therapeutics*, 1993, pp. 820-828, vol. 266.

Suzuki et al., "Involvement of $\delta_1$ and $\delta_2$ Opioid Receptor Subtypes in the Development of Physical Dependence on Morphine in Mice," *Pharmacology Biochemistry and Behavior*, 1997, pp. 293-299, vol. 57, Nos. 1/2.

Suzuki, T. et al., "Effects of a Highly selective Nonpeptide δ opioid Receptor Agonist, TAN-67, on Morphine-induced Antinociception in Mice," *Life Sciences*, Jun. 1995, pp. 155-168, vol. 57, No. 2.

Town et al., "The Opioid Receptor System and Alcoholism: A Genetic Perspective," *European Journal of Pharmacology*, 2000, pp. 243-248, vol. 410, No. 1-2.

Tseng, L.F., "Recent Advances in the Search for the μ-Opioidergic System. The Antinociceptive Properties of Endomorphin-1 and Endomorphin-2 in the Mouse," *Jpn. J. Pharmacol.*, 2002, pp. 216-220, vol. 89, No. 3.

PCT International Search Report and Written Opinion, PCT/US2009/042634, Feb. 24, 2010, 13 Pages.

Martin, T.J., et al., "Antagonism of $\delta_2$-Opioid Receptors by Naltrindole-5'-isothiocyanate Attenuates Heroin Self-Administration but Not Antinociception in Rats," The Journal of Pharmacology and Experimental Therapeutics, May 19, 2000, vol. 294, No. 3, pp. 975-982.

A

B

C

DAMGO HAS NO EFFECT ON DRINKING

D

CTOP SIGNIFICANTLY DECREASES DRINKING

SEQUENCE LISTING

```
<160> NUMBER OF SEQ ID NOS: 2

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
```

-continued

```
<223> OTHER INFORMATION: D-Phe
<220> FEATURE:
<221> NAME/KEY: MOD_RES
<222> LOCATION: (4)..(4)
<223> OTHER INFORMATION: D-Trp
<220> FEATURE:
<221> NAME/KEY: MOD_RES
<222> LOCATION: (5)..(5)
<223> OTHER INFORMATION: Orn
<220> FEATURE:
<221> NAME/KEY: MOD_RES
<222> LOCATION: (7)..(7)
<223> OTHER INFORMATION: Pen
<220> FEATURE:
<223> OTHER INFORMATION: C-term NH2

<400> SEQUENCE: 1

Phe Cys Tyr Trp Xaa Thr Xaa Thr
1               5

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: MOD_RES
<222> LOCATION: (4)..(4)
<223> OTHER INFORMATION: D-Trp
<220> FEATURE:
<221> NAME/KEY: MOD_RES
<222> LOCATION: (7)..(7)
<223> OTHER INFORMATION: Pen
<220> FEATURE:
<223> OTHER INFORMATION: C-term NH2

<400> SEQUENCE: 2

Phe Cys Tyr Trp Arg Thr Xaa Thr
1               5
```

METHODS OF DETERMINING DELTA OPIOID RECEPTOR SUBTYPES

1. CROSS-REFERENCE TO RELATED APPLICATIONS

This application claims priority under 35 U.S.C. 371 to International Application No. PCT/US2009/042634, filed May 1, 2009; which claims the benefit of U.S. Provisional Application No. 61/049,731, filed May 1, 2008, both of which are incorporated herein by reference in their entirety.

Sequence Listing

The instant application contains a Sequence Listing which has been submitted in ASCII format via EFS-Web and is hereby incorporated by reference in its entirety. Said ASCII copy, created on Jan. 2, 2013, is named 15608US_CRF_sequencelisting.txt and is 1,465 bytes in size.

2. GOVERNMENT SUPPORT

The research leading to this invention was supported, at least in part, with funding provided by Grant No. W81XWH-08-1-0017 and W81XWH-08-1-0005 from the United States Department of Defense. The government may have certain rights to the invention.

3. FIELD OF THE INVENTION

The present invention relates to methods of treating or preventing a substance-related disorder using selective delta opioid receptor-1 (DOP-R1) agonists, delta opioid receptor-2 (DOP-R2) antagonists, and/or mu opioid receptor (MOP-R) antagonists, or a pharmaceutically acceptable salt, solvate, hydrate, or prodrug thereof. The methods provided herein comprise administering a therapeutically effective amount of a combination of one or more DOP-R1 agonist and one or more DOP-R2 antagonist and/or one or more MOP-R antagonist. The invention also relates to compositions containing the same.

4. BACKGROUND OF THE INVENTION

According to the National Survey on Drug Use and Health (2004), an estimated 76 million people worldwide have alcohol addiction, including harmful use and dependence. In the United States, the number of people with alcohol addiction is estimated at 10 million.

Many people who would like to quit use of abused agents cannot because they are addicted to one or more dependence-inducing components (e.g., alcohol, nicotine, morphine, cocaine, amphetamine, caffeine, methamphetamine, etc.). Moreover, treatment for substance abuse often involves transfer of dependence to an alternative, but also dependence-inducing agent. Even successful treatment often involves significant and unpleasant withdrawal symptoms.

For example, alcohol dependence constitutes one of the most serious public health problems worldwide. There are only three medications available for the treatment of alcohol dependence: disulfiram, acamprosate, and naltrexone. The opioid antagonist, naltrexone has demonstrated the most consistent effect in reducing alcohol consumption in the context of behavioral therapy (Anton et al., *JAMA* 2006, 295, 2003-17). Naltrexone has been shown to decrease ethanol consumption in numerous animal studies (Altshuler et al., *Life Sci.* 1980, 26, 679-88; Froehlich et al., *Pharmacol. Biochem. Behav.* 1990, 35, 385-90; Stromberg et al., *Alcohol Clin. Exp. Res.* 1998, 22, 2186-91; Stromberg et al., *Alcohol* 2001, 23, 109-16; Volpicelli et al., *Life Sci.* 1986, 38, 841-7) and clinical studies (Anton et al., *J. Clin. Psychopharmacol.* 2001, 21, 72-7; O'Malley et al., *Arch. Gen. Psychiatry* 1992, 49, 881-7; Oslin et al., *Am. J. Geriatr. Psychiatry* 1997, 5, 324-32; Volpicelli et al., *Arch. Gen. Psychiatry* 1992, 49, 876-80) and has been shown to be more effective in heavy or excessive drinkers (Pettinati et al., *J. Clin. Psychopharmacol.* 2006, 26, 610-25). However, not all patients respond to naltrexone and this is partly explained by genetic variations in the mu opioid receptor gene (Oslin et al., *Addict. Biol.* 2006, 11, 397-403). Furthermore, opioid receptor antagonists decrease both ethanol and sucrose intake in rodents (Beczkowska et al., *Brain Res.* 1992, 589, 291-301; Stromberg et al., *Pharmacol. Biochem. Behav.* 2002, 72, 483-90). Alcohol dependence is a complex disorder that will require the use of different therapeutic approaches to effectively treat the disease.

Clearly, there remains a need for improved therapies for alcohol abuse and dependency as well as for substance-related disorders in general.

5. SUMMARY OF THE INVENTION

The present invention provides methods mitigating a substance-related disorder in a mammalian subject in need thereof, comprising administering to the subject an effective amount of a delta opioid receptor-1 (DOP-R1) agonist, an effective amount of a delta opioid receptor-2 (DOP-R2) antagonist, an effective amount of both a DOP-R1 agonist and a DOP-R2 antagonist. Additionally, an effective amount of mu opioid receptor (MOP-R) antagonist may also be administered. In one embodiment the DOP-R1 agonist is chosen from the group consisting of TAN-67, DPDPE. In one embodiment the DOP-R2 antagonist is NTB or 5'-NTII. In another embodiment the MOP-R antagonist is CTOP, β funaltrexamine, CTAP, clocinnamox., etonitazenyl isothiocyanate, naloxonazine, or cyprodime. In an alternative embodiment the mammalian subject is a human.

In one embodiment the substance is alcohol, an opioid or a psychostimulant. In one embodiment the opioid is morphine. In one embodiment the psychostimulant is cocaine.

In another aspect of the invention a pharmaceutical composition comprising a DOP-R1 agonist and a DOP-R2 antagonist is provided. Alternatively, the composition further comprises a MOP-R antagonist. In one embodiment the DOP-R1 agonist is chosen from the group consisting of TAN-67 and DPDPE. In one embodiment the DOP-R2 antagonist is NTB or 5'-NTII. In another embodiment the MOP-R antagonist is CTOP, β funaltrexamine, CTAP, clocinnamox., etonitazenyl isothiocyanate, naloxonazine, or cyprodime.

In another aspect of the invention a method for determining the delta opioid receptor specificity of a candidate agent is provided. The method comprises obtaining a neuronal cell preparation wherein said neuronal cell preparation comprises a delta opioid receptor, exposing said neuronal cell preparation to a candidate agent conditions designed to promote binding of said candidate agent to said receptor; and detecting said binding.

In one embodiment the neuronal cell preparation comprises a neuron known to express an identified delta opioid receptor subtype. In one embodiment detecting the binding comprises detecting bound candidate agent. In one embodiment detecting bound candidate agent comprises detecting an electrophysiological signal. In one embodiment the bound candidate agent is bound to DOP-R1. In another embodiment the bound candidate agent is bound to DOP-R2.

6. BRIEF DESCRIPTION OF DRAWINGS

FIG. 1 provides a graphical representation of experimental results that show non-selective opioid receptor antagonists have only moderate effect on ethanol consumption compared to selective DOP-R2 antagonist, naltriben mexylate (NTB). C57BL/6 mice were injected subcutaneously (s.c.) with vehicle, 5 mg/kg of the non-selective opioid antagonist, naltrexone hydrochloride (NTX), 10 mg/kg of the DOP-R selective antagonist, naltrindole hydrochloride (NTI), or 10 mg/kg of the DOP-R2 antagonist, NTB (FIG. 1A). Thirty minutes after injection ethanol and water consumption was measured over a 4 hour period. A smaller dose of 1.5 mg/kg of NTX resulted in a decrease in consumption, in contrast to a relatively high dose (5 mg/kg), which had only moderate effects on the drinking behavior (FIG. 1B).

Figure 2:
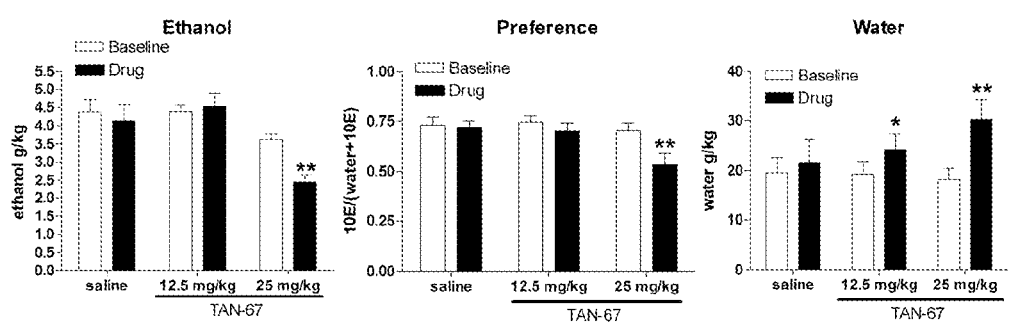

FIG. 2 provides a graphical representation of experimental results that show the DOP-R1 agonist, TAN-67, decreases ethanol consumption. C57BL/6 mice were injected s.c. with vehicle, 12.5 mg/kg or 25 mg/kg of the DOP-R1 agonist, TAN-67. Thirty minutes after injection ethanol and water consumption was measured over a 4 hour period.

Figure 3:
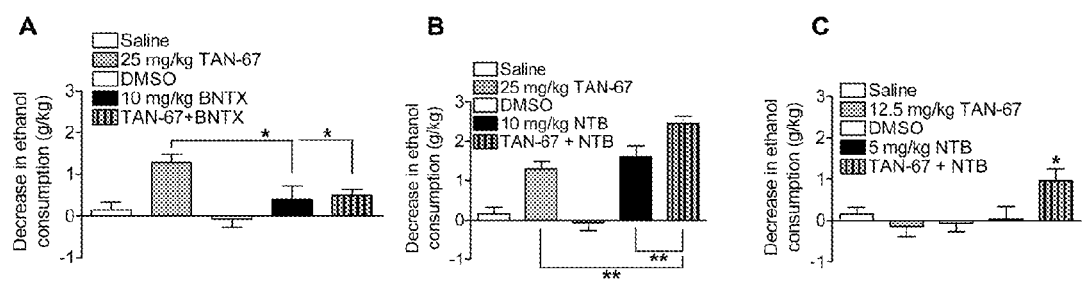

FIG. 3 provides a graphical representation of experimental results that show the DOP-R1 antagonist blocks the effect of TAN-67, whereas the DOP-R2 antagonist NTB enhances the effect. C57BL/6 mice were injected s.c. with vehicle, 25 mg/kg TAN-67, 10 mg/kg BNTX or 25 mg/kg TAN-67+10 mg/kg BNTX (FIG. 3A). C57BL/6 mice were injected s.c. with 5 mg/kg NTB+12.5 mg/kg TAN-67. C, C57BL/6 mice were injected s.c.10 mg/kg NTB+25 mg/kg TAN-67 (FIG. 3B). Thirty minutes after injection ethanol and water consumption was measured over a 4 hour period.

Figure 4:
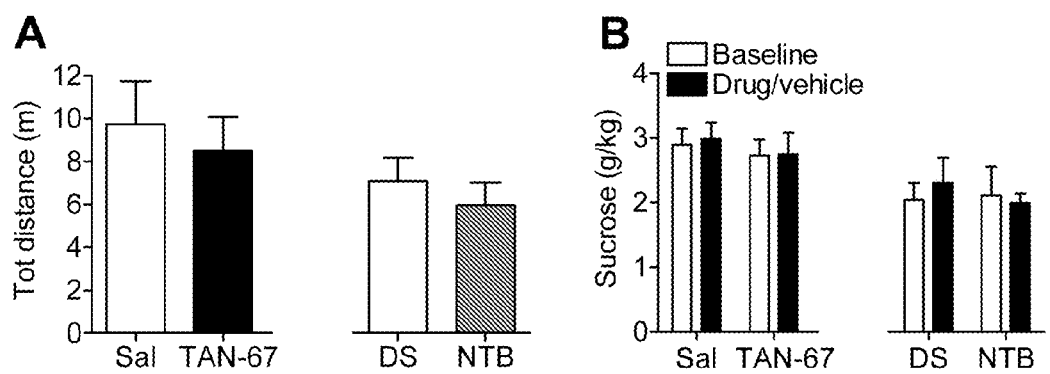

FIG. 4 provides a graphical representation of the experimental results that show that mice injected with 25 mg/kg TAN-67 or 6 mg/kg NTB did not show any significant difference in locomotor activity compared to vehicle treated animals. Neither TAN-67 nor NTB had an effect on sucrose intake.

Figure 5:
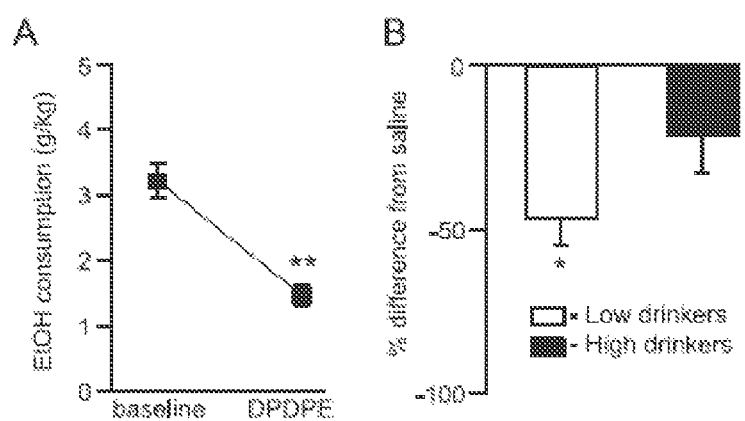
Figure 5:
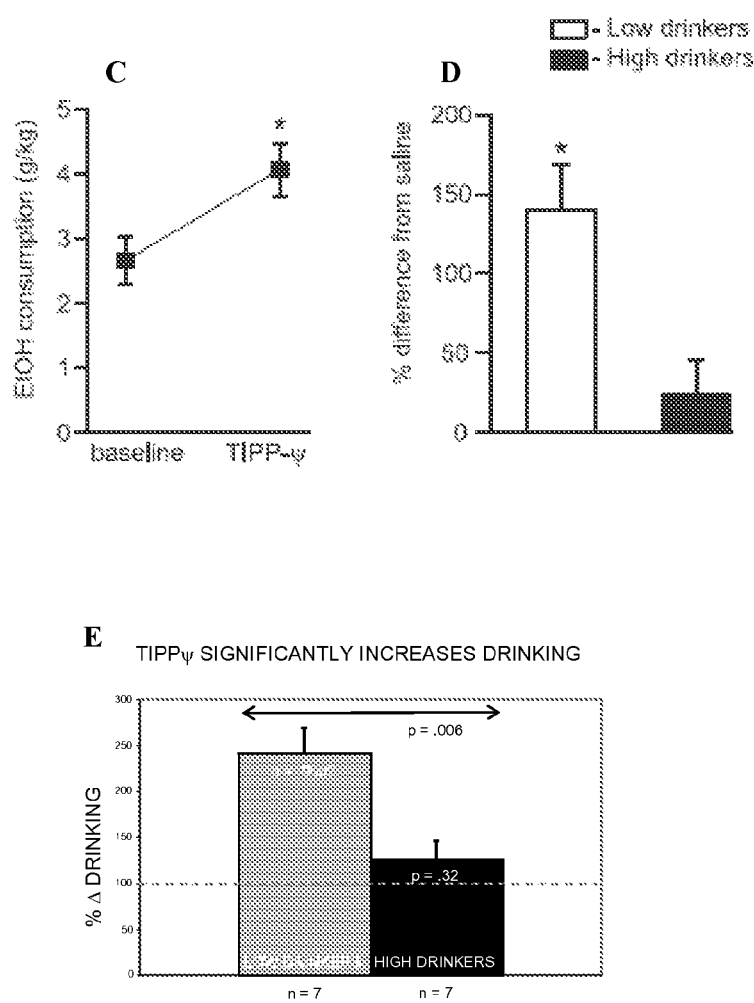

FIG. 5 provides a graphical representation of the experimental results that show TIPP-psi, a DOP-R selective antagonist, injected in the ventral tegmental area (VTA) makes low drinkers drink more. The DOP-R1 selective agonist DPDPE (10 mM) decreased drinking in the animals compared with drinking the day before treatment (FIG. 5A). This effect was particularly prominent in low drinkers while only at trend level in high drinkers (FIG. 5B). The DOP-R selective antagonist TIPP-ψ (5 μM) microinjected into the VTA increased drinking across all animals compared with EtOH consumption the day preceding treatment (FIGS. 5C, D, E).

Figure 6:
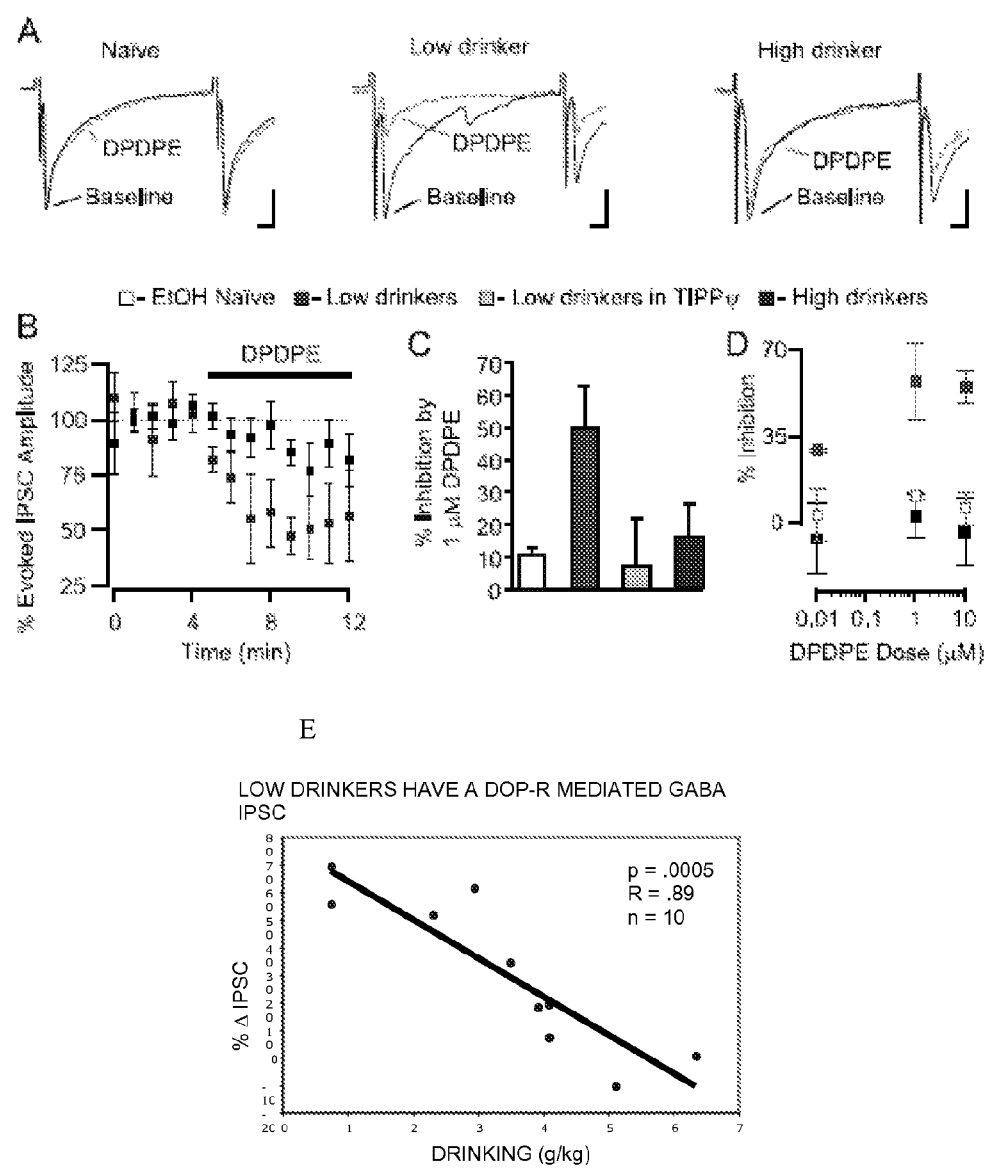

FIG. 6 provides a graphical representation of the experimental results that show DPDPE, a DOP-R1 selective agonist, decreases GABA release in the VTA of low drinkers, but not high drinkers. DPDPE (1 μM) significantly inhibited evoked IPSCs in VTA neurons from drinking animals. In age-matched, ethanol-naive, control animals there was no effect of DPDPE on $GABA_A$ IPSCs (FIGS. 6A, C, D). The DPDPE effect in drinking animals was blocked by the DOP-R selective antagonist TIPP-ψ (1 μM), indicating that the agonist was acting through the DOP-R (FIG. 6C). In the animal groups 1 μM DPDPE was a saturating dose with no apparent shift in the $IC_{50}$ between groups (FIG. 6D).

Figure 7:
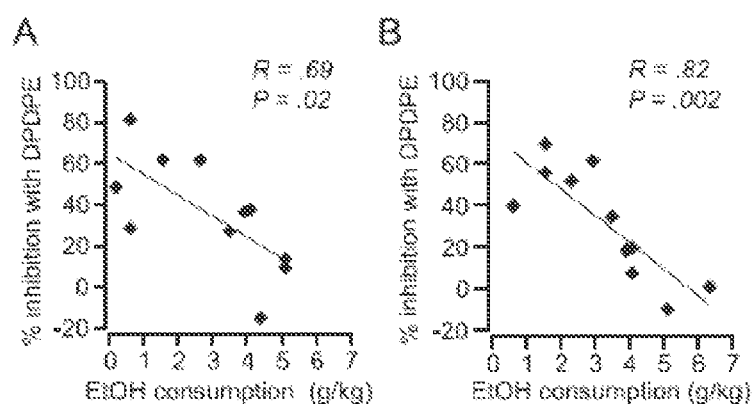

FIG. 7 provides a graphical representation of the experimental results that show that for both evoked IPSCs and spontaneous IPSCs there was an inverse correlation between DPDPE induced inhibition and amount of EtOH consumed, and this relationship was particularly strong for spontaneous IPSC frequency.

Figure 8:
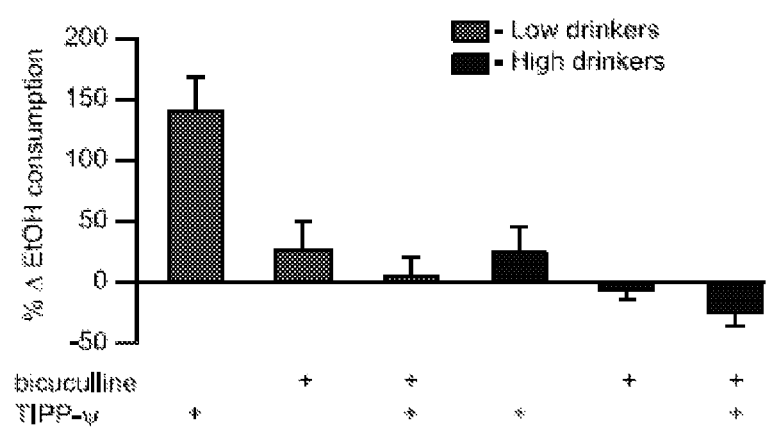

FIG. 8 provides a graphical representation of the experimental results that show that when the $GABA_A$ receptor antagonist bicuculline (1 mM) was coinjected with TIPP-ψ (5 μM) into the VTA, it completely blocked the TIPP-ψ induced increase in EtOH consumption in low-drinking animals. Bicuculline also produced a small overall decrease in drinking across all animals following coadministration, but a median split revealed that this effect was carried by high-drinking animals. TIPP-ψ and bicuculline cotreatment had no effect on EtOH consumption in low-drinking animals.

Figure 9:
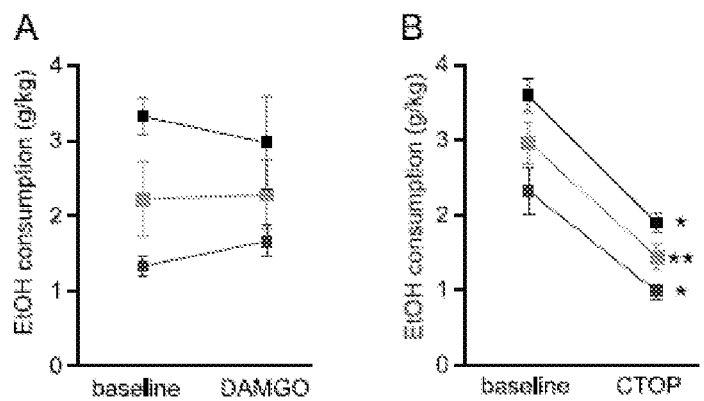
Figure 9:
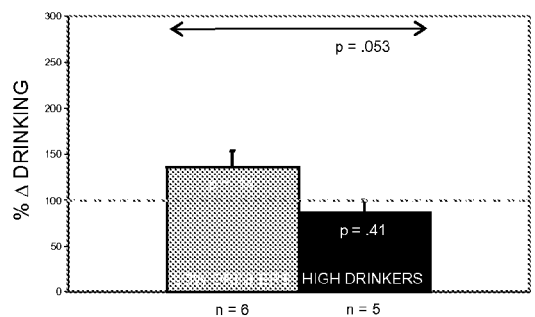
Figure 9:
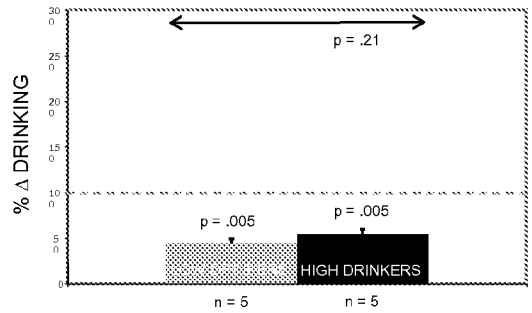

FIG. 9 provides a graphical representation of the experimental results that show CTOP, a MOP-R selective antagonist, injected in the VTA decreases drinking in all animals. Microinjection of DAMGO (0.2 mM) into the VTA did not affect drinking (FIGS. 13A, C) while CTOP (10 mM) significantly decreased drinking (FIG. 9B, D).

Figure 10:
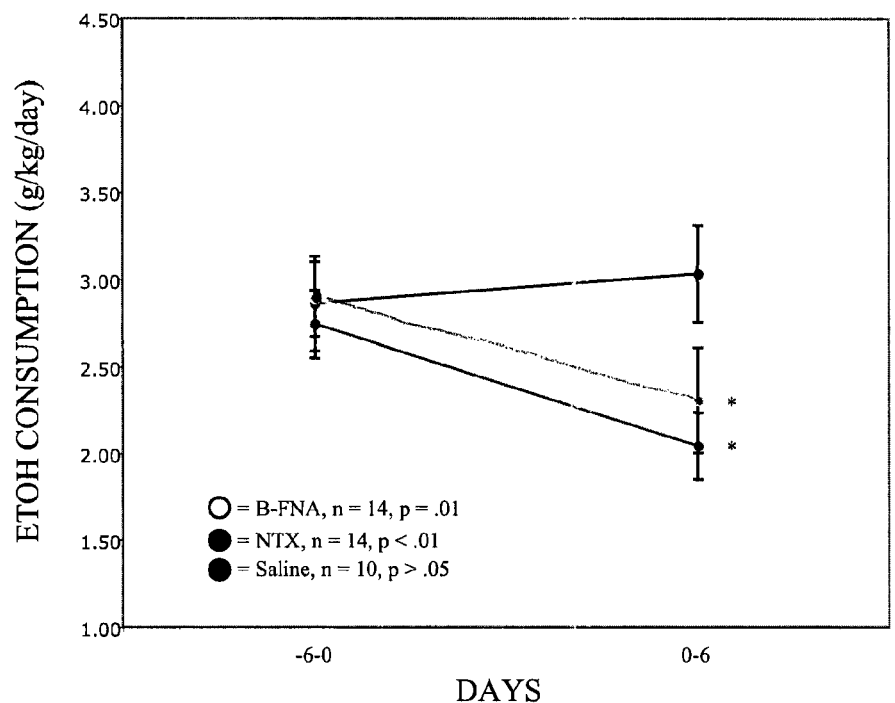

FIG. 10 provides a graphical representation of the experimental results that show chronically drinking rats decrease their drinking after systemic administration of the mu opioid antagonist beta-FNA.

Figure 11:
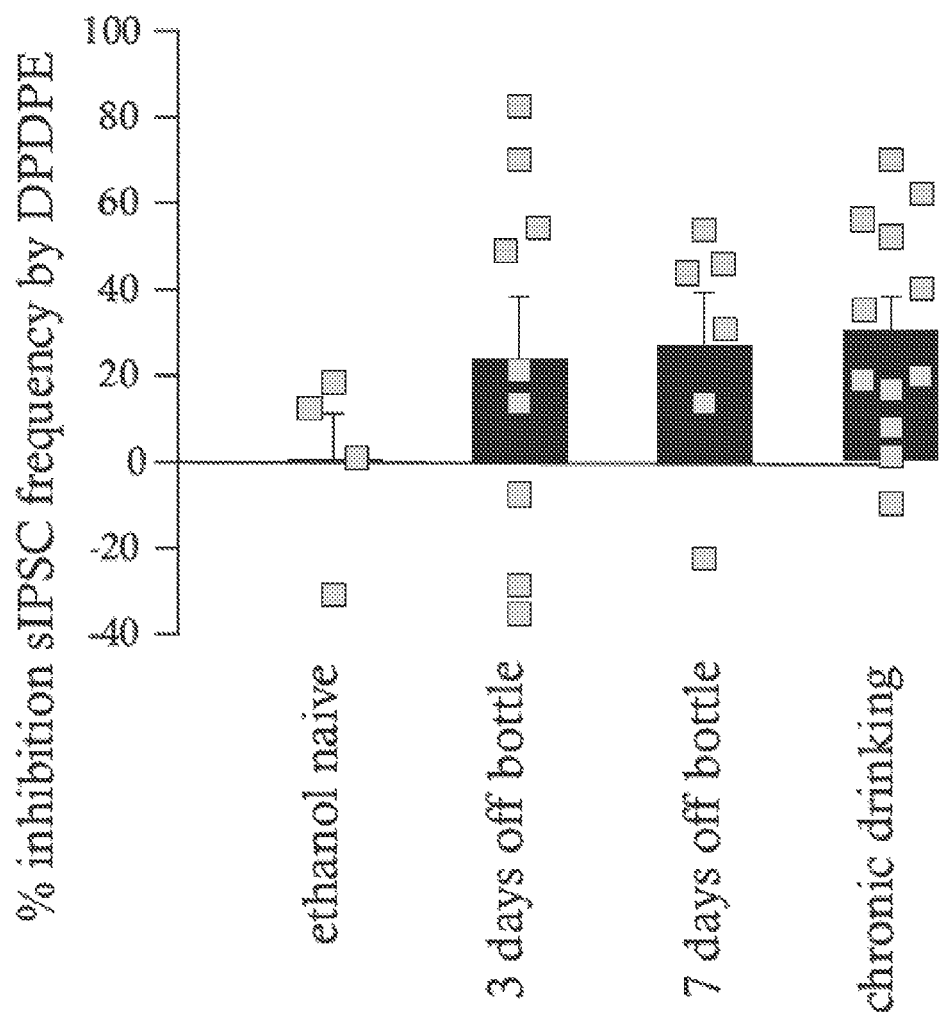

FIG. 11 provides a graphical representation of the experimental results that show DPDPE effects on GABA release at 3 and 7 days off bottles. At both time points DPDPE maintained its ability to inhibit GABA release onto VTA neurons.

Figure 12:
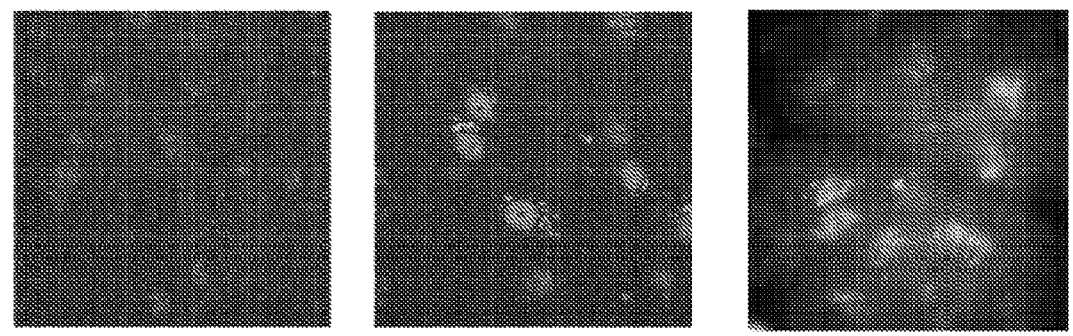
Figure 12:
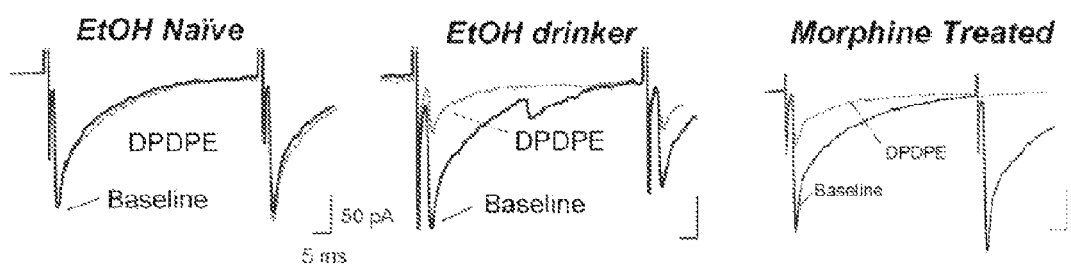
Figure 12:
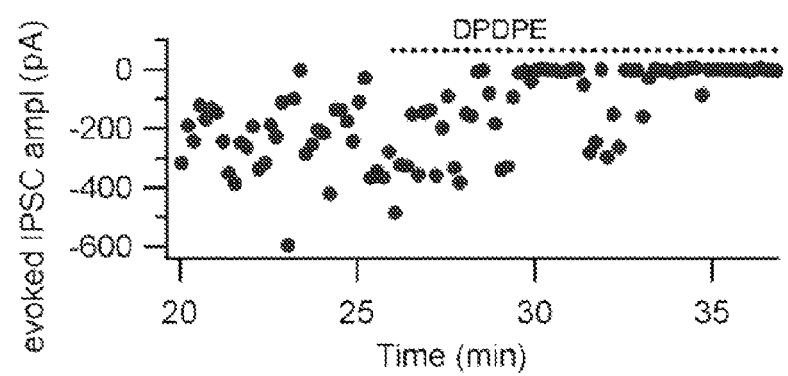

FIG. 12 provides a graphical representation of the experimental results that show that DOR expression increases in the VTA following both chronic drinking and chronic morphine treatment. Electrophysiological measurements made in VTA neurons show that in morphine-treated animals, as in drinking animals, activating DOR1 inhibits electrically evoked GABA release.

7. DETAILED DESCRIPTION OF THE INVENTION

7.1 Definitions

As used herein, the following terms shall have the following meanings:

The terms "treat," "treating" or "treatment," as used herein, refer to a method of alleviating or abrogating a disorder and/or its attendant symptoms. The terms "prevent," "preventing" or "prevention," in certain embodiments, refer to a method of barring a subject from acquiring a disorder and/or its attendant symptoms. In certain embodiments, the terms "prevent," "preventing," or "prevention," refer to a method of reducing the risk of acquiring a disorder and/or its attendant symptoms.

The term "mitigate" as used herein means to treat or prevent. It can encompass amelioration or elimination of the underlying condition.

The term "detecting a bound agent" refers to the use of any of a number of well-known techniques for assaying binding of an agent to a receptor. Detecting a bound agent is intended encompass all manner of binding assays to determine the amount, kinetics, equilibrium binding constants, and the like associated with a biochemical binding reaction. Detecting bound agent can accomplished using techniques well known to those of skill in the art including radioimmunoassay, ELISA, competition ELISA, sandwich ELISA, Calcium imaging, direct detection of binding using labeled ligands such as, e.g., radio labeled and fluorescent labeled ligands.

The term "subject" refers to animals such as mammals, including, but not limited to, primates (e.g., humans), cows, sheep, goats, horses, dogs, cats, rabbits, rats, mice and the like. In preferred embodiments, the subject is a human.

The term "effective amount" is meant to include the amount of a compound that, when administered, is sufficient to prevent development of, or alleviate to some extent, one or more of the symptoms of the disorder, disease, or condition being treated. The term "effective amount" also refers to the amount of a compound that is sufficient to elicit the biological or medical response of a cell, tissue, system, animal, or human, which is being sought by a researcher, veterinarian, medical doctor, or clinician. It is well within the level or ordinary to determine an effective amount such as by, e.g., evaluating dose-response relationships to determine parameters such as, e.g., an ED50, and LD50, an IC50 or the like, wherein such parameters refer to the dose producing an effected, lethality or inhibition at the 50$^{th}$ percentile.

The term "substance-related disorder" refers to a Substance Use Disorder known to practitioners of skill in the art such as Substance Dependence, Substance Craving and Substance Abuse; Substance-Induced Disorders such as Substance Intoxication, Substance Withdrawal, Substance-Induced Delirium, Substance-Induced Persisting Dementia, Substance-Induced Persisting Amnestic Disorder, Substance-Induced Psychotic Disorder, Substance-Induced Mood Disorder, Substance-Induced Anxiety Disorder, Substance-Induced Sexual Dysfunction, Substance-Induced Sleep Disorder and Hallucinogen Persisting Perception Disorder (Flashbacks); Alcohol-Related Disorders such as Alcohol Dependence (303.90), Alcohol Abuse (305.00), Alcohol Intoxication (303.00), Alcohol Withdrawal (291.81), Alcohol Intoxication Delirium, Alcohol Withdrawal Delirium, Alcohol-Induced Persisting Dementia, Alcohol-Induced Persisting Amnestic Disorder, Alcohol-Induced Psychotic Disorder, Alcohol-Induced Mood Disorder, Alcohol-Induced Anxiety Disorder, Alcohol-Induced Sexual Dysfunction, Alcohol-Induced Sleep Disorder and Alcohol-Related Disorder Not Otherwise Specified (291.9); Amphetamine (or Amphetamine-like)-Related Disorders such as Amphetamine Dependence (304.40), Amphetamine Abuse (305.70), Amphetamine Intoxication (292.89), Amphetamine Withdrawal (292.0), Amphetamine Intoxication Delirium, Amphetamine Induced Psychotic Disorder, Amphetamine-Induced Mood Disorder, Amphetamine-Induced Anxiety Disorder, Amphetamine-Induced Sexual Dysfunction, Amphetamine-Induced Sleep Disorder and Amphetamine-Related Disorder Not Otherwise Specified (292.9); a Caffeine Related Disorder such as Caffeine Intoxication (305.90), Caffeine-Induced Anxiety Disorder, Caffeine-Induced Sleep Disorder and Caffeine-Related Disorder Not Otherwise Specified (292.9); a *Cannabis*-Related Disorder such as *Cannabis* Dependence (304.30), *Cannabis* Abuse (305.20), *Cannabis* Intoxication (292.89), *Cannabis* Intoxication Delirium, *Cannabis*-induced Psychotic Disorder, *Cannabis*-induced Anxiety Disorder and *Cannabis*-Related Disorder Not Otherwise Specified (292.9); a Cocaine-Related Disorder such as Cocaine Dependence (304.20), Cocaine Abuse (305.60), Cocaine Intoxication (292.89), Cocaine Withdrawal (292.0), Cocaine Intoxication Delirium, Cocaine-Induced Psychotic Disorder, Cocaine-Induced Mood Disorder, Cocaine-Induced Anxiety Disorder, Cocaine-Induced Sexual Dysfunction, Cocaine-Induced Sleep Disorder and Cocaine-Related Disorder Not Otherwise Specified (292.9); Hallucinogen-Related Disorders such as Hallucinogen Dependence (304.50), Hallucinogen Abuse (305.30), Hallucinogen Intoxication (292.89), Hallucinogen Persisting Perception Disorder (Flashbacks) (292.89), Hallucinogen Intoxication Delirium, Hallucinogen-Induced Psychotic Disorder, Hallucinogen-Induced Mood Disorder, Hallucinogen-Induced Anxiety Disorder and Hallucinogen-Related Disorder Not Otherwise Specified (292.9); an Inhalant-Related Disorders such as Inhalant Dependence (304.60), Inhalant Abuse (305.90), Inhalant Intoxication (292.89), Inhalant Intoxication Delirium, Inhalant-Induced Persisting Dementia, Inhalant-Induced Psychotic Disorder, Inhalant-Induced Mood Disorder, Inhalant-Induced Anxiety Disorder and Inhalant-Related Disorder Not Otherwise Specified (292.9); Nicotine-Related Disorders such as Nicotine Dependence (305.1), Nicotine Withdrawal (292.0) and Nicotine-Related Disorder Not Otherwise Specified (292.9); Opioid-Related Disorders such as Opioid Dependence (304.00), Opioid Abuse (305.50), Opioid Intoxication (292.89), Opioid Withdrawal (292.0), Opioid Intoxication Delirium, Opioid-induced Psychotic Disorder, Opioid-induced Mood Disorder, Opioid-induced Sexual Dysfunction, Opioid-induced Sleep Disorder and Opioid-Related Disorder Not Otherwise Specified (292.9); Morphine-Related Disorders such as Morphine Dependence, Morphine Abuse, Morphine Intoxication, Morphine Withdrawal, Morphine Intoxication Delirium, Morphine-induced Psychotic Disorder, Morphine-induced Mood Disorder, Morphine-induced Sexual Dysfunction, Morphine-induced Sleep Disorder and Morphine-Related Disorder Not Otherwise Specified; a Phencyclidine (or Phencyclidine-Like)-Related Disorder such as Phencyclidine Dependence (304.60), Phencyclidine Abuse (305.90), Phencyclidine Intoxication (292.89), Phencyclidine Intoxication Delirium, Phencyclidine-induced Psychotic Disorder, Phencyclidine-induced Mood Disorder, Phencyclidine-induced Anxiety Disorder and Phencyclidine-Related Disorder Not Otherwise Specified (292.9); Sedative-, Hypnotic-, or Anxiolytic-Related Disorders such as Sedative, Hypnotic, or Anxiolytic Dependence (304.10), Sedative, Hypnotic, or Anxiolytic Abuse (305.40), Sedative, Hypnotic, or Anxiolytic Intoxication (292.89), Sedative, Hypnotic, or Anxiolytic Withdrawal (292.0), Sedative, Hypnotic, or Anxiolytic Intoxication Delirium, Sedative, Hypnotic, or Anxiolytic Withdrawal Delirium, Sedative-, Hypnotic-, or Anxiolytic-Persisting Dementia, Sedative-, Hypnotic-, or Anxiolytic-Persisting Amnestic Disorder, Sedative-, Hypnotic-, or Anxiolytic-induced Psychotic Disorder, Sedative-, Hypnotic-, or Anxiolytic-induced Mood Disorder, Sedative-, Hypnotic-, or Anxiolytic-induced Anxiety Disorder, Sedative-, Hypnotic-, or Anxiolytic-induced Sexual Dysfunction, Sedative-, Hypnotic-, or Anxiolytic-induced Sleep Disorder and Sedative-, Hypnotic-, or Anxiolytic-Related Disorder Not Otherwise Specified (292.9); Polysubstance-Related Disorder such as Polysubstance Dependence (304.80); and another (or Unknown) Substance-Related Disorder induced by Anabolic Steroids, Nitrate Inhalants and Nitrous Oxide. The terms describing the indications used herein are classified in the Diagnostic and Statistical Manual of Mental Disorders, 4th Edition, published by the American Psychiatric Association (DSM-IV); the "Diagnostic and Statistical Manual of Mental Disorders, Fourth Edition, Text Revision (DSM-IV-TR)", Washington, D.C., American Psychiatric Association, 2000; and/or the International Classification of Diseases, 10th Edition (ICD-10). The contents of all are hereby incorporated by reference in their entireties. The various subtypes of the disorders mentioned herein are contemplated as part of the present invention. Numbers in brackets after the listed diseases above refer to the classification code in DSM-IV.

The term "substance" as used herein refers to a substance that causes a substance-related disorder. Substances include, but are not limited to alcohol, amphetamine or similarly acting sympathomimetics, caffeine, *cannabis*, cocaine, hallucinogens, inhalants, nicotine, opioids, phencyclidine (PCP) or similarly acting arylcyclohexylamines, sedatives, hypnotics, anxiolytics or medications such as anesthetics, analgesics, anticholinergic agents, anticonvulsants, antihistamines, antihypertensive and cardiovascular medications, antimicrobial medications, anti-parkinsonian medications, chemotherapeutic agents, corticosteroids, gastrointestinal medications, muscle relaxants, nonsteroidal anti-inflammatory medications, other over-the-counter medications, antidepressant medications, and disulfiram. In another embodiment substances which can lead to the development of a substance-related disorder are toxic substances such as but not limited to heavy metals (e.g., lead or aluminum) rat poisons containing strychnine, pesticides containing nicotine, or acetylcholine-esterase inhibitors, nerve gases, ethylene glycol (antifreeze), carbon monoxide, and carbon dioxide. In yet another embodiment substances which can lead to the development of a substance-related disorder are volatile substances or "inhalants" (e.g., fuel, paint) if they are used for the purpose of becoming intoxicated; they are considered toxins if exposure is accidental or part of intentional poisoning.

The term "opioid" or "opioids" as used herein refers to a natural or synthetic substance that have opiate-like activities. Opioids or opiates include, but are not limited to alfentanil, allylprodine, alphaprodine, anileridine, benzylmorphine, bezitramide, buprenorphine, butorphanol, clonitazene, codeine, cyclazocine, desomorphine, dextromoramide, dezocine, diampromide, diamorphone, dihydrocodeine, dihydromorphine, dimenoxadol, dimepheptanol, dimethylthiambutene, dioxaphetylbutyrate, dipipanone, eptazocine, ethoheptazine, ethylmethylthiambutene, ethylmorphine, etonitazene fentanyl, heroin, hydrocodone, hydromorphone, hydroxypethidine, isomethadone, ketobemidone, levallorphan, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, propheptazine, promedol, properidine, propiram, propoxyphene, sufentanil, tilidine, and tramadol.

The term "withdrawal" as used herein refers to the development of a substance-specific maladaptive behavioral change, with physiological and cognitive concomitants, that is due to the cessation of, reduction in, heavy and prolonged substance use. This substance-specific syndrome can cause clinically significant distress or impairment in social, occupational, or other important areas of functioning. The symptoms are not due to a general medical condition and are not accounted for by any other mental disorder. Withdrawal is usually, but not always, associated with Substance Dependence. Most (perhaps all) individuals with withdrawal have a craving to readminister the substance to reduce the symptoms. The diagnosis of withdrawal is recognized, but not limited to the following groups of substances: alcohol; amphetamines and other related substances; cocaine; nicotine; opioids; and sedatives, hypnotics, and anxiolytics. The dose and duration of use and other factors such as the presence or absence of additional illnesses also affect withdrawal symptoms.

The term "addiction-related behavior" as used herein refers to behavior resulting from compulsive substance use and is characterized by apparent substance dependency.

The term "substance dependency" or "substance dependence" as used herein refers to a condition of a subject displaying a maladaptive pattern of substance use, leading to clinically significant impairment or distress, as manifested by three (or more) of the following apparent to a practitioner of skill in the art, occurring any time in the same 12-month period:
(1) tolerance, as defined by either of the following:
 (a) a need for markedly increased amounts of the substance to achieve intoxication or desired effect
 (b) markedly diminished effect with continued use of the same amount of the substance
(2) withdrawal, as manifested by either of the following:
 (a) the characteristic withdrawal syndrome for the substance (development of a substance-specific syndrome due to the cessation of (or reduction in) substance use that has been heavy and prolonged, wherein the substance-specific syndrome causes clinically significant distress or impairment in social, occupational, or other important areas of functioning)
 (b) the same (or a closely related) substance is taken to relieve or avoid withdrawal symptoms
(3) the substance is often taken in larger amounts or over a longer period than was intended
(4) there is a persistent desire or unsuccessful efforts to cut down or control substance use
(5) a great deal of time is spent in activities necessary to obtain the substance (e.g. visiting multiple doctors or driving long distances), use the substance (e.g. chain smoking), or recover from its effects
(6) important social, occupational, or recreational activities are given up or reduced because of substance use
(7) the substance use is continued despite the knowledge of having a persistent or recurrent physical or psychological problem that is likely to have been caused or exacerbated by the substance (e.g. current cocaine use despite recognition of cocaine induced depression, or continued drinking despite recognition that an ulcer was made worse by alcohol consumption)

The term "alcohol" and "ethanol" as used herein are interchangeable.

The term "alcohol abuse" as used herein refers to a condition of a subject displaying a maladaptive pattern of alcohol use leading to clinically significant impairment or distress, as manifested by one (or more) of the following apparent to a practitioner of skill in the art occurring within a 12-month period: recurrent alcohol use resulting in a failure to fulfill major role obligations at work, school, or home (e.g., school and job performance may suffer either from the aftereffects of drinking or from actual intoxication on the job or at school; child care or household responsibilities may be neglected; and alcohol-related absences may occur from job or school); recurrent alcohol use in situations in which it is physically hazardous (e.g., driving an automobile or operating machinery while intoxicated); recurrent alcohol-related legal problems (e.g., arrests for intoxicated behavior or for driving under the influence); continued alcohol use despite having persistent or recurrent social or interpersonal problems caused or exacerbated by the effects of the substance (e.g., violent arguments with spouse while intoxicated, child abuse). Alcohol abuse requires fewer symptoms and, thus, may be less severe than dependence and is only diagnosed once the absence of dependence has been established.

The term "alcohol withdrawal" as used herein refers to a condition of a subject fulfilling the following diagnostic criteria as judged by a practitioner of skill in the art:
(1) Cessation of (or reduction in) alcohol use that has been heavy and prolonged.
(2) Two (or more) of the following, developing within several hours to a few days after Criterion (1):

(a) autonomic hyperactivity (e.g., sweating or pulse rate greater than 100)
(b) increased hand tremor
(c) insomnia
(d) nausea or vomiting
(e) transient visual, tactile, or auditory hallucinations or illusions
(f) psychomotor agitation
(g) anxiety
(h) grand mal seizures
(3) The symptoms in Criterion (2) cause clinically significant distress or impairment in social, occupational, or other important areas of functioning.
(4) The symptoms are not due to a general medical condition and are not better accounted for by another mental disorder.

The term "delta opioid receptor-1 agonist" includes pharmaceutically acceptable salts, solvates, hydrates and prodrugs thereof.

The term "delta opioid receptor-2 antagonist" includes pharmaceutically acceptable salts, solvates, hydrates and prodrugs thereof.

The term "mu opioid receptor antagonist" includes pharmaceutically acceptable salts, solvates, hydrates and prodrugs thereof.

The term "solvate" as used herein, refers to a compound, agent, or small molecule of the present invention that is complexed to a solvent. Solvents that can form solvates with the compounds, agents, and small molecules of the present invention include common organic solvents such as alcohols (methanol, ethanol, etc.), ethers, acetone, ethyl acetate, halogenated solvents (methylene chloride, chloroform, etc.), hexane and pentane. Additional solvents include water. When water is the complexing solvent, the complex is termed a "hydrate."

As used herein, the term "small molecules" refers to small organic or inorganic molecules of molecular weight below 5,000 Daltons. In one embodiment small molecules useful for the invention have a molecular weight of less than 1,000 Daltons. In one embodiment small molecules useful for the invention have a molecular weight of less than 500 Daltons.

The term "pharmaceutically acceptable carrier," "pharmaceutically acceptable excipient," "physiologically acceptable carrier," or "physiologically acceptable excipient" refers to a pharmaceutically-acceptable material, composition, or vehicle, such as a liquid or solid filler, diluent, excipient, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, *Remington: The Science and Practice of Pharmacy*, 21st Edition; Lippincott Williams & Wilkins: Philadelphia, Pa., 2005; *Handbook of Pharmaceutical Excipients*, 5th Edition; Rowe et al., Eds., The Pharmaceutical Press and the American Pharmaceutical Association: 2005; and *Handbook of Pharmaceutical Additives*, 3rd Edition; Ash and Ash Eds., Gower Publishing Company: 2007; *Pharmaceutical Preformulation and Formulation*, Gibson Ed., CRC Press LLC: Boca Raton, Fla., 2004).

The term "psychostimulant" is a compound that interacts with the dopaminergic system to act either as an agonist or as a reuptake inhibitor. Examples include cocaine, amphetamine, methamphetamine as well as empathogens such as ecstasy.

7.2 Methods of Use

In one embodiment provided herein are methods for the treatment or prevention of a substance-related disorder in a subject in need thereof comprising administering to the subject an amount of one or more DOP-R1 agonists, or a pharmaceutically acceptable salt, solvate, hydrate, or prodrug thereof.

In one embodiment provided herein are methods for the treatment or prevention of a substance-related disorder in a subject in need thereof comprising administering to the subject an amount of one or more DOP-R1 agonists in combination with one or more DOP-R2 antagonists and/or MOP-R antagonists, or a pharmaceutically acceptable salt, solvate, hydrate, or prodrug thereof.

In certain embodiments provided herein are methods for the treatment or prevention of a substance-related disorder in a subject in need thereof comprising administering to the subject a pharmaceutical composition comprising a pharmaceutically acceptable carrier and an amount of one or more DOP-R1 agonists, or a pharmaceutically acceptable salt, solvate, hydrate, or prodrug thereof, and an amount of one or more DOP-R2 antagonists, or a pharmaceutically acceptable salt, solvate, hydrate, or prodrug thereof, effective to treat or prevent the substance-related disorder.

In certain embodiments provided herein are methods for the treatment or prevention of a substance-related disorder in a subject in need thereof comprising administering to the subject an amount of one or more DOP-R1 agonists, or a pharmaceutically acceptable salt, solvate, hydrate, or prodrug thereof, and an amount of one or more MOP-R antagonists, or a pharmaceutically acceptable salt, solvate, hydrate, or prodrug thereof, effective to treat or prevent the substance-related disorder.

In certain embodiments provided herein are methods for the treatment or prevention of a substance-related disorder in a subject in need thereof comprising administering to the subject an amount of one or more DOP-R1 agonists, or a pharmaceutically acceptable salt, solvate, hydrate, or prodrug thereof, and an amount of one or more DOP-R2 antagonists, or a pharmaceutically acceptable salt, solvate, hydrate, or prodrug thereof, and an amount of one or more MOP-R antagonists, or a pharmaceutically acceptable salt, solvate, hydrate, or prodrug thereof, effective to treat or prevent the substance-related disorder.

In certain embodiments provided herein are methods for the treatment or prevention of a substance-related disorder in a subject in need thereof comprising administering to the subject an amount of one or more DOP-R2 antagonists, or a pharmaceutically acceptable salt, solvate, hydrate, or prodrug thereof, and an amount of one or more MOP-R antagonists, or a pharmaceutically acceptable salt, solvate, hydrate, or prodrug thereof, effective to treat or prevent the substance-related disorder.

In certain embodiments, the substance causing a substance-related disorder in a subject includes, but is not limited to alcohol, amphetamine or similarly acting sympathomimetics, caffeine, *cannabis*, cocaine, hallucinogens, inhalants, nicotine, opioids, phencyclidine (PCP) or similarly acting arylcyclohexylamines, sedatives, hypnotics, medications such as anesthetics, analgesics, anti-parkinsonian medications, gastrointestinal medications, other over-the-counter medications, and antidepressant medications. In another embodiment the substance causing the substance-related disorder in a subject includes but is not limited to opioids (e.g., morphine). In another embodiment the substance causing the substance-related disorder in a subject includes but is not limited to pesticides containing nicotine, or ethylene glycol (antifreeze). In yet another embodiment the substance causing the substance-related disorder includes, but is not limited to volatile substances or "inhalants", such as fuel or glue, if they are used for the purpose of becoming intoxicated.

In certain embodiments, the substance causing a substance-related disorder in a subject is alcohol.

In certain embodiments, the substance-related disorder is alcohol abuse.

In certain embodiments, the substance-related disorder is opioid abuse.

In certain embodiments, the substance-related disorder is morphine abuse.

In one embodiment provided herein are methods of ameliorating or eliminating effects of a substance-related disorder in a subject in need thereof, comprising administering to the subject an amount of one or more DOP-R1 agonists, or a pharmaceutically acceptable salt, solvate, hydrate, or prodrug thereof, effective to ameliorate or eliminate the effects of the substance-related disorder.

In one embodiment provided herein are methods of ameliorating or eliminating effects of a substance-related disorder in a subject in need thereof, comprising administering to the subject an amount of one or more DOP-R1 agonists in combination with one or more DOP-R2 antagonists and/or MOP-R antagonists, or a pharmaceutically acceptable salt, solvate, hydrate, or prodrug thereof, effective to ameliorate or eliminate the effects of the substance-related disorder.

In certain embodiments provided herein are methods of ameliorating or eliminating effects of a substance-related disorder in a subject in need thereof, comprising administering to the subject an amount of one or more DOP-R1 agonists, or a pharmaceutically acceptable salt, solvate, hydrate, or prodrug thereof, and an amount of one or more DOP-R2 antagonists, or a pharmaceutically acceptable salt, solvate, hydrate, or prodrug thereof, effective to ameliorate or eliminate the effects of the substance-related disorder.

In certain embodiment provided herein are methods of ameliorating or eliminating effects of a substance-related disorder in a subject in need thereof, comprising administering to the subject an amount of one or more DOP-R1 agonists, or a pharmaceutically acceptable salt, solvate, hydrate, or prodrug thereof, and an amount of one or more MOP-R antagonists, or a pharmaceutically acceptable salt, solvate, hydrate, or prodrug thereof, effective to ameliorate or eliminate the effects of the substance-related disorder.

In certain embodiment provided herein are methods of ameliorating or eliminating effects of a substance-related disorder in a subject in need thereof, comprising administering to the subject an amount of one or more DOP-R1 agonists, or a pharmaceutically acceptable salt, solvate, hydrate, or prodrug thereof, and an amount of one or more DOP-R2 antagonists, or a pharmaceutically acceptable salt, solvate, hydrate, or prodrug thereof, and an amount of one or more MOP-R antagonists, or a pharmaceutically acceptable salt, solvate, hydrate, or prodrug thereof, effective to ameliorate or eliminate the effects of the substance-related disorder.

In certain embodiment provided herein are methods of ameliorating or eliminating effects of a substance-related disorder in a subject in need thereof, comprising administering to the subject an amount of one or more DOP-R2 antagonists, or a pharmaceutically acceptable salt, solvate, hydrate, or prodrug thereof, and an amount of one or more MOP-R antagonists, or a pharmaceutically acceptable salt, solvate, hydrate, or prodrug thereof, effective to ameliorate or eliminate the effects of the substance-related disorder.

In certain embodiments, the effects of a substance-related disorder include, but are not limited to significant impairment or distress caused by a maladaptive pattern of substance use. The significant impairment or distress is manifested including, but not limited to recurrent substance use resulting in a failure to fulfill major role obligations at work, school, or home (e.g., repeated absences or poor work performance related to substance use; substance-related absences, suspensions, or expulsions from school; neglect of children or household); recurrent substance use in situations in which it is physically hazardous (e.g., driving an automobile or operating a machine when impaired by substance use); recurrent substance-related legal problems (e.g., arrests for substance-related disorderly conduct); continued substance use despite having persistent or recurrent social or interpersonal problems caused or exacerbated by the effects of the substance (e.g., arguments with spouse about consequences of intoxication, physical fights).

In an additional embodiment, the effects of a substance-related disorder include, but are not limited to those biochemical or behavioral changes that occur as a result of and within a reasonable time frame following the administration of the substance. Different effects can be expected depending on the substance and the dose administered thereof. For example, the effects of low doses of ethanol include locomotor activation whereas the effects of high doses of ethanol include symptoms of alcohol intoxication (for definition of alcohol intoxication, see American Psychiatric Association, Diagnostic Criteria for DSM-IV, Washington D.C, 2000, p. 214f).

In one embodiment provided herein are methods for diminishing, inhibiting, or eliminating an addiction-related behavior in a subject suffering from a substance-related disorder comprising administering to the subject an amount of one or more DOP-R1 agonists, or a pharmaceutically acceptable salt, solvate, hydrate, or prodrug thereof, effective to diminish, inhibit or eliminate the addiction-related behavior.

In one embodiment provided herein are methods for diminishing, inhibiting, or eliminating an addiction-related behavior in a subject suffering from a substance-related disorder comprising administering to the subject an amount of one or more DOP-R1 agonists in combination with DOP-R2 antagonists and/or MOP-R antagonists, or a pharmaceutically acceptable salt, solvate, hydrate, or prodrug thereof, effective to diminish, inhibit or eliminate the addiction-related behavior.

In one embodiment provided herein are methods for diminishing, inhibiting, or eliminating an addiction-related behavior in a subject suffering from a substance-related disorder comprising administering to the subject an amount of one or more DOP-R1 agonists, or a pharmaceutically acceptable salt, solvate, hydrate, or prodrug thereof, and an amount of one or more DOP-R2 antagonists, or a pharmaceutically acceptable salt, solvate, hydrate, or prodrug thereof, effective to diminish, inhibit or eliminate the addiction-related behavior.

In one embodiment provided herein are methods for diminishing, inhibiting, or eliminating an addiction-related behavior in a subject suffering from a substance-related disorder comprising administering to the subject an amount of one or more DOP-R1 agonists, or a pharmaceutically acceptable salt, solvate, hydrate, or prodrug thereof, and an amount of one or more MOP-R antagonists, or a pharmaceutically acceptable salt, solvate, hydrate, or prodrug thereof, effective to diminish, inhibit or eliminate the addiction-related behavior.

In one embodiment provided herein are methods for diminishing, inhibiting, or eliminating an addiction-related behavior in a subject suffering from a substance-related disorder comprising administering to the subject an amount of one or more DOP-R1 agonists, or a pharmaceutically acceptable salt, solvate, hydrate, or prodrug thereof, and an amount of one or more DOP-R2 antagonists, or a pharmaceutically acceptable salt, solvate, hydrate, or prodrug thereof, and an amount of one or more MOP-R antagonists, or a pharmaceutically acceptable salt, solvate, hydrate, or prodrug thereof, effective to diminish, inhibit or eliminate the addiction-related behavior.

In one embodiment provided herein are methods for diminishing, inhibiting, or eliminating an addiction-related behavior in a subject suffering from a substance-related disorder comprising administering to the subject an amount of one or more DOP-R2 antagonists, or a pharmaceutically acceptable salt, solvate, hydrate, or prodrug thereof, and an amount of one or more MOP-R antagonists, or a pharmaceutically acceptable salt, solvate, hydrate, or prodrug thereof, effective to diminish, inhibit or eliminate the addiction-related behavior.

In certain embodiments, the DOP-R1 agonists useful in the methods include, but are not limited to peptide agonists, such as (2-D-penicillamine, 5-D-penicillamine)-enkephalin (DP-DPE), and non-peptide agonists, such as 2-methyl-4 alpha alpha-(3-hydroxyphenyl)-1,2,3,4,4a,5,12,12 alpha alpha-octahydro-quinolino[2,3,3,-g]isoquinoline (TAN-67). These and other DOP-R1 agonists will be readily apparent to those skilled in the art.

In certain embodiments, DOP-R2 antagonists useful in the methods include, but are not limited to naltriben (NTB) and naltrindole 5'-isothiocyanate (5'-NTII). These and other DOP-R2 antagonists will be readily apparent to those skilled in the art.

In certain embodiments, MOP-R antagonists useful in the methods include, but are not limited to D-Phe-Cys-Tyr-D-Trp-Orn-Thr-Pen-Thr-NH2 (CTOP) (SEQ ID NO: 1), D-Phe-Cys-Tyr-D-Trp-Arg-Thr-Pen-Thr-NH2 (CTAP) (SEQ ID NO: 2), β-funaltrexamine (β-FNA), clocinnamox, etonitazenyl isothiocyanate, naloxonazine, and (−)—N-(Cyclopropylmethyl)-4,14-dimethoxymorphinan-6-one (cyprodime). These and other MOP-R antagonists will be readily apparent to those skilled in the art.

In preferred embodiments herein the subject is a human.

In certain embodiments, DOP-R1 agonists, or a pharmaceutically acceptable salt, solvate, hydrate, or prodrug thereof, can be administered in any form deemed suitable by a practitioner of skill in the art and by any technique deemed suitable by the same. Exemplary forms and techniques for administration are provided herein.

In one embodiment, a DOP-R1 agonist is administered to a subject suffering from a substance-related disorder in a dosage range of 0.1 to 300 mg per day.

In one embodiment, a DOP-R1 agonist is administered to a subject suffering from a substance-related disorder in a dosage range of 0.1 to 150 mg per day.

In one embodiment, a DOP-R1 agonist is administered to a subject suffering from a substance-related disorder in a dosage range of 0.1 to 50 mg per day.

In one embodiment, a DOP-R1 agonist is administered to a subject suffering from a substance-related disorder in a dosage range of 0.1 to 20 mg per day.

In certain embodiments, DOP-R2 antagonists, or a pharmaceutically acceptable salt, solvate, hydrate, or prodrug thereof, can be administered in any form deemed suitable by a practitioner of skill in the art and by any technique deemed suitable by the same. Exemplary forms and techniques for administration are provided herein.

In one embodiment, a DOP-R2 antagonist is administered to a subject suffering from a substance-related disorder in a dosage range of 0.1 to 300 mg per day.

In one embodiment, a DOP-R2 antagonist is administered to a subject suffering from a substance-related disorder in a dosage range of 0.1 to 150 mg per day.

In one embodiment, a DOP-R2 antagonist is administered to a subject suffering from a substance-related disorder in a dosage range of 0.1 to 50 mg per day.

In one embodiment, a DOP-R2 antagonist is administered to a subject suffering from a substance-related disorder in a dosage range of 0.1 to 20 mg per day.

In certain embodiments, MOP-R antagonists, or a pharmaceutically acceptable salt, solvate, hydrate, or prodrug thereof, can be administered in any form deemed suitable by a practitioner of skill in the art and by any technique deemed suitable by the same. Exemplary forms and techniques for administration are provided herein.

In one embodiment, a MOP-R antagonist is administered to a subject suffering from a substance-related disorder in a dosage range of 0.1 to 300 mg per day.

In one embodiment, a MOP-R antagonist is administered to a subject suffering from a substance-related disorder in a dosage range of 0.1 to 150 mg per day.

In one embodiment, a MOP-R antagonist is administered to a subject suffering from a substance-related disorder in a dosage range of 0.1 to 50 mg per day.

In one embodiment, a MOP-R antagonist is administered to a subject suffering from a substance-related disorder in a dosage range of 0.1 to 20 mg per day.

In certain embodiments, DOP-R2 antagonists, or a pharmaceutically acceptable salt, solvate, hydrate, or prodrug thereof, can be administered together with DOP-R1 agonists, or a pharmaceutically acceptable salt, solvate, hydrate, or prodrug thereof, in any form deemed suitable by a practitioner of skill in the art and by any technique deemed suitable by the same. Exemplary forms and techniques for administration are provided herein.

In one embodiment, one or more DOP-R1 agonists and DOP-R2 antagonists are administered to a subject suffering from a substance-related disorder in a dosage range as described above.

In certain embodiments, MOP-R antagonists, or a pharmaceutically acceptable salt, solvate, hydrate, or prodrug thereof, can be administered together with DOP-R1 agonists, or a pharmaceutically acceptable salt, solvate, hydrate, or prodrug thereof, in any form deemed suitable by a practitioner of skill in the art and by any technique deemed suitable by the same. Exemplary forms and techniques for administration are provided herein.

In one embodiment, one or more DOP-R1 agonists and MOP-R antagonists are administered to a subject suffering from a substance-related disorder in a dosage range as described above.

In certain embodiments, MOP-R antagonists, or a pharmaceutically acceptable salt, solvate, hydrate, or prodrug thereof, can be administered together with DOP-R2 antagonists, or a pharmaceutically acceptable salt, solvate, hydrate, or prodrug thereof, in any form deemed suitable by a practitioner of skill in the art and by any technique deemed suitable by the same. Exemplary forms and techniques for administration are provided herein.

In one embodiment, one or more DOP-R2 antagonists and MOP-R antagonists are administered to a subject suffering from a substance-related disorder in a dosage range as described above.

In certain embodiments, MOP-R antagonists, or a pharmaceutically acceptable salt, solvate, hydrate, or prodrug thereof, can be administered together with DOP-R1 agonists, or a pharmaceutically acceptable salt, solvate, hydrate, or prodrug thereof, and DOP-R2 antagonists, or a pharmaceutically acceptable salt, solvate, hydrate, or prodrug thereof, in any form deemed suitable by a practitioner of skill in the art and by any technique deemed suitable by the same. Exemplary forms and techniques for administration are provided herein.

In one embodiment, one or more DOP-R1 agonists, DOP-R2 antagonists, and MOP-R antagonists are administered to a subject suffering from a substance-related disorder in a dosage range as described above.

In one embodiment, TAN-67 and NTB are administered together to a subject suffering from a substance-related disorder in dosage ranges described above.

In one embodiment, TAN-67 and 5'-NTII are administered together to a subject suffering from a substance-related disorder in dosage ranges described above.

In one embodiment, TAN-67 and CTOP are administered together to a subject suffering from a substance-related disorder in dosage ranges described above.

In one embodiment, TAN-67 and CTAP are administered together to a subject suffering from a substance-related disorder in dosage ranges described above.

In one embodiment, TAN-67 and β-FNA are administered together to a subject suffering from a substance-related disorder in dosage ranges described above.

In one embodiment, TAN-67 and clocinnamox are administered together to a subject suffering from a substance-related disorder in dosage ranges described above.

In one embodiment, TAN-67 and etonitazenyl isothiocyanate are administered together to a subject suffering from a substance-related disorder in dosage ranges described above.

In one embodiment, TAN-67 and naloxonazine are administered together to a subject suffering from a substance-related disorder in dosage ranges described above.

In one embodiment, TAN-67 and cyprodime are administered together to a subject suffering from a substance-related disorder in dosage ranges described above.

In one embodiment, DPDPE and NTB are administered together to a subject suffering from a substance-related disorder in dosage ranges described above.

In one embodiment, DPDPE and 5'-NTII are administered together to a subject suffering from a substance-related disorder in dosage ranges described above.

In one embodiment, DPDPE and CTOP are administered together to a subject suffering from a substance-related disorder in dosage ranges described above.

In one embodiment, DPDPE and CTAP are administered together to a subject suffering from a substance-related disorder in dosage ranges described above.

In one embodiment, DPDPE and β-FNA are administered together to a subject suffering from a substance-related disorder in dosage ranges described above.

In one embodiment, DPDPE and clocinnamox are administered together to a subject suffering from a substance-related disorder in dosage ranges described above.

In one embodiment, DPDPE and etonitazenyl isothiocyanate are administered together to a subject suffering from a substance-related disorder in dosage ranges described above.

In one embodiment, DPDPE and naloxonazine are administered together to a subject suffering from a substance-related disorder in dosage ranges described above.

In one embodiment, DPDPE and cyprodime are administered together to a subject suffering from a substance-related disorder in dosage ranges described above.

In one embodiment, NTB and CTOP are administered together to a subject suffering from a substance-related disorder in dosage ranges described above.

In one embodiment, NTB and CTAP are administered together to a subject suffering from a substance-related disorder in dosage ranges described above.

In one embodiment, NTB and β-FNA are administered together to a subject suffering from a substance-related disorder in dosage ranges described above.

In one embodiment, NTB and clocinnamox are administered together to a subject suffering from a substance-related disorder in dosage ranges described above.

In one embodiment, NTB and etonitazenyl isothiocyanate are administered together to a subject suffering from a substance-related disorder in dosage ranges described above.

In one embodiment, NTB and naloxonazine are administered together to a subject suffering from a substance-related disorder in dosage ranges described above.

In one embodiment, NTB and cyprodime are administered together to a subject suffering from a substance-related disorder in dosage ranges described above.

In one embodiment, 5'-NTII and CTOP are administered together to a subject suffering from a substance-related disorder in dosage ranges described above.

In one embodiment, 5'-NTII and CTAP are administered together to a subject suffering from a substance-related disorder in dosage ranges described above.

In one embodiment, 5'-NTII and β-FNA are administered together to a subject suffering from a substance-related disorder in dosage ranges described above.

In one embodiment, 5'-NTII and clocinnamox are administered together to a subject suffering from a substance-related disorder in dosage ranges described above.

In one embodiment, 5'-NTII and etonitazenyl isothiocyanate are administered together to a subject suffering from a substance-related disorder in dosage ranges described above.

In one embodiment, 5'-NTII and naloxonazine are administered together to a subject suffering from a substance-related disorder in dosage ranges described above.

In one embodiment, 5'-NTII and cyprodime are administered together to a subject suffering from a substance-related disorder in dosage ranges described above.

In one embodiment, TAN-67, DPDPE, and NTB are administered together to a subject suffering from a substance-related disorder in dosage ranges described above.

In one embodiment, TAN-67, DPDPE, and 5'-NTII are administered together to a subject suffering from a substance-related disorder in dosage ranges described above.

In one embodiment, TAN-67, DPDPE, and cyprodime are administered together to a subject suffering from a substance-related disorder in dosage ranges described above.

In one embodiment, TAN-67, DPDPE, and CTOP are administered together to a subject suffering from a substance-related disorder in dosage ranges described above.

In one embodiment, TAN-67, DPDPE, and CTAP are administered together to a subject suffering from a substance-related disorder in dosage ranges described above.

In one embodiment, TAN-67, DPDPE, and β-FNA are administered together to a subject suffering from a substance-related disorder in dosage ranges described above.

In one embodiment, TAN-67, DPDPE, NTB, and cyprodime are administered together to a subject suffering from a substance-related disorder in dosage ranges described above.

In one embodiment, TAN-67, DPDPE, NTB, and CTOP are administered together to a subject suffering from a substance-related disorder in dosage ranges described above.

In one embodiment, TAN-67, DPDPE, NTB, and CTAP are administered together to a subject suffering from a substance-related disorder in dosage ranges described above.

In one embodiment, TAN-67, DPDPE, NTB, and 5'-NTII are administered together to a subject suffering from a substance-related disorder in dosage ranges described above.

In one embodiment, TAN-67, DPDPE, NTB, and β-FNA are administered together to a subject suffering from a substance-related disorder in dosage ranges described above.

In one embodiment, TAN-67, DPDPE, NTB, β-FNA, and cyprodime are administered together to a subject suffering from a substance-related disorder in dosage ranges described above.

In one embodiment, TAN-67, DPDPE, NTB, β-FNA, and CTOP are administered together to a subject suffering from a substance-related disorder in dosage ranges described above.

In one embodiment, TAN-67, DPDPE, NTB, β-FNA, and CTAP are administered together to a subject suffering from a substance-related disorder in dosage ranges described above.

In one embodiment, TAN-67, DPDPE, NTB, cyprodime, CTOP, and CTAP are administered together to a subject suffering from a substance-related disorder in dosage ranges described above.

In one embodiment, TAN-67, DPDPE, 5'-NTII, and cyprodime are administered together to a subject suffering from a substance-related disorder in dosage ranges described above. In one embodiment, TAN-67, DPDPE, 5'-NTII, and CTOP are administered together to a subject suffering from a substance-related disorder in dosage ranges described above.

In one embodiment, TAN-67, DPDPE, 5'-NTII, and CTAP are administered together to a subject suffering from a substance-related disorder in dosage ranges described above.

In one embodiment, TAN-67, DPDPE, 5'-NTII, and β-FNA are administered together to a subject suffering from a substance-related disorder in dosage ranges described above.

In one embodiment, TAN-67, DPDPE, 5'-NTII, β-FNA, and cyprodime are administered together to a subject suffering from a substance-related disorder in dosage ranges described above.

In one embodiment, TAN-67, DPDPE, 5'-NTII, β-FNA, and CTOP are administered together to a subject suffering from a substance-related disorder in dosage ranges described above.

In one embodiment, TAN-67, DPDPE, 5'-NTII, β-FNA, and CTAP are administered together to a subject suffering from a substance-related disorder in dosage ranges described above.

In one embodiment, TAN-67, DPDPE, 5'-NTII, cyprodime, CTAP, and CTOP are administered together to a subject suffering from a substance-related disorder in dosage ranges described above.

In one embodiment, TAN-67, DPDPE, NTB, 5'-NTII, and cyprodime are administered together to a subject suffering from a substance-related disorder in dosage ranges described above.

In one embodiment, TAN-67, DPDPE, NTB, 5'-NTII, and CTOP are administered together to a subject suffering from a substance-related disorder in dosage ranges described above.

In one embodiment, TAN-67, DPDPE, NTB, 5'-NTII, and CTAP are administered together to a subject suffering from a substance-related disorder in dosage ranges described above.

In one embodiment, TAN-67, DPDPE, NTB, 5'-NTII, and β-FNA are administered together to a subject suffering from a substance-related disorder in dosage ranges described above.

In one embodiment, TAN-67, DPDPE, NTB, 5'-NTII, β-FNA, and cyprodime are administered together to a subject suffering from a substance-related disorder in dosage ranges described above.

In one embodiment, TAN-67, DPDPE, NTB, 5'-NTII, β-FNA, and CTOP are administered together to a subject suffering from a substance-related disorder in dosage ranges described above.

In one embodiment, TAN-67, DPDPE, NTB, 5'-NTII, β-FNA, and cyprodime are administered together to a subject suffering from a substance-related disorder in dosage ranges described above.

In one embodiment, TAN-67, DPDPE, NTB, 5'-NTII, CTOP, and cyprodime are administered together to a subject suffering from a substance-related disorder in dosage ranges described above.

In one embodiment, TAN-67, DPDPE, NTB, 5'-NTII, CTAP, and cyprodime are administered together to a subject suffering from a substance-related disorder in dosage ranges described above.

In one embodiment, TAN-67, DPDPE, NTB, 5'-NTII, β-FNA, and CTAP are administered together to a subject suffering from a substance-related disorder in dosage ranges described above.

In one embodiment, TAN-67, DPDPE, NTB, 5'-NTII, CTAP, and CTOP are administered together to a subject suffering from a substance-related disorder in dosage ranges described above.

In one embodiment, TAN-67, DPDPE, NTB, 5'-NTII, β-FNA, CTAP, and CTOP are administered together to a subject suffering from a substance-related disorder in dosage ranges described above.

In one embodiment, TAN-67, NTB, and 5'-NTII are administered together to a subject suffering from a substance-related disorder in dosage ranges described above.

In one embodiment, TAN-67, NTB, and cyprodime are administered together to a subject suffering from a substance-related disorder in dosage ranges described above.

In one embodiment, TAN-67, NTB, and CTOP are administered together to a subject suffering from a substance-related disorder in dosage ranges described above.

In one embodiment, TAN-67, NTB, and CTAP are administered together to a subject suffering from a substance-related disorder in dosage ranges described above.

In one embodiment, TAN-67, NTB, and β-FNA are administered together to a subject suffering from a substance-related disorder in dosage ranges described above.

In one embodiment, TAN-67, NTB, β-FNA, and cyprodime are administered together to a subject suffering from a substance-related disorder in dosage ranges described above.

In one embodiment, TAN-67, NTB, β-FNA, and CTOP are administered together to a subject suffering from a substance-related disorder in dosage ranges described above.

In one embodiment, TAN-67, NTB, β-FNA, and CTAP are administered together to a subject suffering from a substance-related disorder in dosage ranges described above.

In one embodiment, TAN-67, NTB, cyprodime, CTOP, and CTAP are administered together to a subject suffering from a substance-related disorder in dosage ranges described above.

In one embodiment, TAN-67, 5'-NTII, and cyprodime are administered together to a subject suffering from a substance-related disorder in dosage ranges described above.

In one embodiment, TAN-67, 5'-NTII, and CTOP are administered together to a subject suffering from a substance-related disorder in dosage ranges described above.

In one embodiment, TAN-67, 5'-NTII, and CTAP are administered together to a subject suffering from a substance-related disorder in dosage ranges described above.

In one embodiment, TAN-67, 5'-NTII, and β-FNA are administered together to a subject suffering from a substance-related disorder in dosage ranges described above.

In one embodiment, TAN-67, 5'-NTII, β-FNA, and cyprodime are administered together to a subject suffering from a substance-related disorder in dosage ranges described above.

In one embodiment, TAN-67, 5'-NTII, CTOP, and cyprodime are administered together to a subject suffering from a substance-related disorder in dosage ranges described above.

In one embodiment, TAN-67, 5'-NTII, CTAP, and cyprodime are administered together to a subject suffering from a substance-related disorder in dosage ranges described above.

In one embodiment, TAN-67, 5'-NTII, β-FNA, and CTOP are administered together to a subject suffering from a substance-related disorder in dosage ranges described above.

In one embodiment, TAN-67, 5'-NTII, β-FNA, and CTAP are administered together to a subject suffering from a substance-related disorder in dosage ranges described above.

In one embodiment, TAN-67, 5'-NTII, cyprodime, CTAP, and CTOP are administered together to a subject suffering from a substance-related disorder in dosage ranges described above.

In one embodiment, TAN-67, β-FNA, and cyprodime are administered together to a subject suffering from a substance-related disorder in dosage ranges described above.

In one embodiment, TAN-67, CTOP, and cyprodime are administered together to a subject suffering from a substance-related disorder in dosage ranges described above.

In one embodiment, TAN-67, CTAP, and cyprodime are administered together to a subject suffering from a substance-related disorder in dosage ranges described above.

In one embodiment, TAN-67, β-FNA, and CTOP are administered together to a subject suffering from a substance-related disorder in dosage ranges described above.

In one embodiment, TAN-67, β-FNA, and CTAP are administered together to a subject suffering from a substance-related disorder in dosage ranges described above.

In one embodiment, TAN-67, cyprodime, CTAP, and CTOP are administered together to a subject suffering from a substance-related disorder in dosage ranges described above.

In one embodiment, TAN-67, β-FNA, cyprodime, CTAP, and CTOP are administered together to a subject suffering from a substance-related disorder in dosage ranges described above.

In one embodiment, DPDPE, NTB, and 5'-NTII are administered together to a subject suffering from a substance-related disorder in dosage ranges described above.

In one embodiment, DPDPE, NTB, and cyprodime are administered together to a subject suffering from a substance-related disorder in dosage ranges described above.

In one embodiment, DPDPE, NTB, and CTOP are administered together to a subject suffering from a substance-related disorder in dosage ranges described above.

In one embodiment, DPDPE, NTB, and CTAP are administered together to a subject suffering from a substance-related disorder in dosage ranges described above.

In one embodiment, DPDPE, NTB, and β-FNA are administered together to a subject suffering from a substance-related disorder in dosage ranges described above.

In one embodiment, DPDPE, NTB, β-FNA, and cyprodime are administered together to a subject suffering from a substance-related disorder in dosage ranges described above.

In one embodiment, DPDPE, NTB, CTOP, and cyprodime are administered together to a subject suffering from a substance-related disorder in dosage ranges described above.

In one embodiment, DPDPE, NTB, CTAP, and cyprodime are administered together to a subject suffering from a substance-related disorder in dosage ranges described above.

In one embodiment, DPDPE, NTB, β-FNA, and CTOP are administered together to a subject suffering from a substance-related disorder in dosage ranges described above.

In one embodiment, DPDPE, NTB, β-FNA, and CTAP are administered together to a subject suffering from a substance-related disorder in dosage ranges described above.

In one embodiment, DPDPE, NTB, CTAP, and CTOP are administered together to a subject suffering from a substance-related disorder in dosage ranges described above.

In one embodiment, DPDPE, 5'-NTII, and cyprodime are administered together to a subject suffering from a substance-related disorder in dosage ranges described above.

In one embodiment, DPDPE, 5'-NTII, and CTOP are administered together to a subject suffering from a substance-related disorder in dosage ranges described above.

In one embodiment, DPDPE, 5'-NTII, and CTAP are administered together to a subject suffering from a substance-related disorder in dosage ranges described above.

In one embodiment, DPDPE, 5'-NTII, and β-FNA are administered together to a subject suffering from a substance-related disorder in dosage ranges described above.

In one embodiment, DPDPE, 5'-NTII, β-FNA, and cyprodime are administered together to a subject suffering from a substance-related disorder in dosage ranges described above.

In one embodiment, DPDPE, 5'-NTII, CTOP, and cyprodime are administered together to a subject suffering from a substance-related disorder in dosage ranges described above.

In one embodiment, DPDPE, 5'-NTII, CTAP, and cyprodime are administered together to a subject suffering from a substance-related disorder in dosage ranges described above.

In one embodiment, DPDPE, 5'-NTII, β-FNA, and CTOP are administered together to a subject suffering from a substance-related disorder in dosage ranges described above.

In one embodiment, DPDPE, 5'-NTII, β-FNA, and CTAP are administered together to a subject suffering from a substance-related disorder in dosage ranges described above.

In one embodiment, DPDPE, 5'-NTII, CTAP, and CTOP are administered together to a subject suffering from a substance-related disorder in dosage ranges described above.

In one embodiment, DPDPE, β-FNA, and cyprodime are administered together to a subject suffering from a substance-related disorder in dosage ranges described above.

In one embodiment, DPDPE, CTOP, and cyprodime are administered together to a subject suffering from a substance-related disorder in dosage ranges described above.

In one embodiment, DPDPE, CTAP, and cyprodime are administered together to a subject suffering from a substance-related disorder in dosage ranges described above.

In one embodiment, DPDPE, β-FNA, and CTOP are administered together to a subject suffering from a substance-related disorder in dosage ranges described above.

In one embodiment, DPDPE, β-FNA, and CTAP are administered together to a subject suffering from a substance-related disorder in dosage ranges described above.

In one embodiment, DPDPE, CTAP, and CTOP are administered together to a subject suffering from a substance-related disorder in dosage ranges described above.

In one embodiment, DPDPE, β-FNA, CTAP, and CTOP are administered together to a subject suffering from a substance-related disorder in dosage ranges described above.

One skilled in the art would recognize that the combinations listed above are examples and not exhaustive. One skilled in the art would readily recognize that other DOP-R1 agonists, DOP-R2 antagonists, and MOP-R antagonists may be combined in any fashion that is therapeutically effective in administering to a subject suffering from a substance-related disorder.

7.3 Delta Opioid Receptor-1 Agonists, Delta Opioid Receptor-2 Antagonists, and Mu Opioid Receptor Antagonists Delta opioid receptor-1 agonists may be peptides or non-peptide small molecules designed to selectively target the delta opioid receptor-1 pathway, which has been shown to modulate the transmission of afferent nociceptive neural activity (see Aronin et al., *J. Neurosci.* 1981, 1, 561-577; Dickenson et al., *Brain Res.* 1987, 413, 36-44; Miller and Seybold, *J. Comp. Neurol.* 1989, 279, 619-628; Ramabandran et al., *Crit. Rev. Neurobiol.* 1990, 6, 13-32; Levine et al., *J. Neurosci.* 1993, 13, 2272-2286; Standifer et al., *Neuron* 1994, 12, 805-810; Narita and Tseng, *J. Pharmacol.* 1995, 284, 185-189; Acosta and Lopez, *J. Neurosci.* 1999, 19, 8337-8348). It is believed that peptide agonists, such as (2-D-penicillamine, 5-D-penicillamine)-enkephalin (DPDPE), and non-peptide agonists, such as 2-methyl-4 alpha alpha-(3-hydroxyphenyl)-1,2,3,4,4a,5,12,12 alpha alpha-octahydroquinolino[2,3,3,-g]isoquinoline (TAN-67), selectively agonize the delta opioid receptor-1 pathway (See Suzuki et al., *Life Sci.* 1995, 57, 155-168; Kamei et al., *Eur. J. Pharmacol.* 1995, 276, 131-135; Knapp et al., *Eur. J. Pharmacol.* 1995, 291, 129-134).

Delta opioid receptor-2 antagonists may be peptides or non-peptide small molecules designed to selectively target the delta opioid receptor-2 pathway, which has been shown to affect acute dependence on morphine in mice, alcohol intake in rats, and antinociception (see Miyamoto Y. et al., *J. Pharmacol. Exp. Ther.* 1993, 264, 1141-1145; Miyamoto Y. et al., *J. Pharmacol. Exp. Ther.* 1993, 265, 1325-1327; Krishnan-Sarin et al., *Pharmacol. Biochem. Behav.* 1995, 52, 153-159; June et al., *Psychopharmacology (Berl).* 1999, 147, 81-89; Stewart and Hammond, *J. Pharmacol. Exp. Ther.* 1993, 266, 820-828). It is believed that antagonists, such as naltriben (NTB) and naltrindole 5'-isothiocyanate (5'-NTII), selectively antagonize the delta opioid receptor-2 pathway (see Suzuki et al., *Pharmacol. Biochem. Behav.* 1997, 57, 293-299).

Mu opioid receptor antagonists may be peptides or non-peptide small molecules designed to selectively target the mu opioid receptor pathway, which has been shown to affect acute dependence on morphine in mice, alcohol intake in rats, and antinociception (see Town et al., *Eur. J. Pharmacol.* 2000, 410, 243-248; Pasternak, *Life Sci.* 2001, 68, 2213-2219; Tseng, *Jpn. J. Pharmacol.* 2002, 89, 216-220). It is believed that antagonists, such as D-Phe-Cys-Tyr-D-Trp-Orn-Thr-Pen-Thr-NH2 (CTOP) (SEQ ID NO: 1), D-Phe-Cys-Tyr-D-Trp-Arg-Thr-Pen-Thr-NH2 (CTAP) (SEQ ID NO: 2), β-funaltrexamine (β-FNA), clocinnamox, etonitazenyl isothiocyanate, naloxonazine, and (−)—N-(Cyclopropylmethyl)-4,14-dimethoxymorphinan-6-one (cyprodime) antagonize the mu opioid receptor pathway (see Gulya et al., *Eur. J. Pharmacol.* 1988, 150, 355-360; Hayes et al., *J. Pharm. Pharmacol.* 1985, 37, 841-843; Chan et al., *Eur. J. Pharmacol.* 1995, 287, 135-143; Rios and Tephly, *Drug Metab. Dispos.* 2002, 30, 1364-1367; Kamei et al., *Neurosci. Lett.* 1994, 165, 141-143; Schmidhammer et al., *J. Med. Chem.* 1989, 32, 418-421).

In certain embodiments a DOP-R1 agonist and/or a DOP-R2 antagonist may be provided as a pharmaceutically acceptable salt deemed suitable by one of skill in the art (see, Berge et al., *J. Pharm. Sci.* 1977, 66, 1-19; and "Handbook of Pharmaceutical Salts, Properties, and Use," Stahl and Wermuth, Ed.; Wiley-VCH and VHCA, Zurich, 2002).

Suitable acids for use in the preparation of pharmaceutically acceptable salts include, but are not limited to, acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxoglutaric acid, glycolic acid, hippuric acid, hydrobromic acid, hydrochloric acid, hydroiodic acid, (+)-L-lactic acid, (±)-DL-lactic acid, lactobionic acid, lauric acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, L-pyroglutamic acid, saccharic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid, undecylenic acid, and valeric acid.

In one embodiment, the preferred acid to form a pharmaceutically acceptable salt of a DOP-R1 agonist and/or a DOP-R2 antagonist is hydrochloric acid or methanesulfonic acid.

In certain embodiments, a DOP-R1 agonist and/or a DOP-R2 antagonist may also be provided as a prodrug, which is a functional derivative of the compound and is readily convertible into the parent compound in vivo. Prodrugs are often useful because, in some situations, they may be easier to administer than the parent compound. They may, for instance, be bioavailable by oral administration whereas the parent compound is not. The prodrug may also have enhanced solubility in pharmaceutical compositions over the parent compound. A prodrug may be converted into the parent drug by various mechanisms, including enzymatic processes and metabolic hydrolysis. See Harper, *Progress in Drug Research* 1962, 4, 221-294; Morozowich et al. in "Design of Biopharmaceutical Properties through Prodrugs and Analogs," Roche Ed., APHA Acad. Pharm. Sci. 1977; "Bioreversible Carriers in Drug in Drug Design, Theory and Application," Roche Ed., APHA Acad. Pharm. Sci. 1987; "Design of Prodrugs," Bundgaard, Elsevier, 1985; Wang et al., *Curr. Pharm. Design* 1999, 5, 265-287; Pauletti et al., *Adv. Drug. Delivery Rev.* 1997, 27, 235-256; Mizen et al., *Pharm. Biotech.* 1998, 11, 345-365; Gaignault et al., *Pract. Med. Chem.* 1996, 671-696;

Asgharnejad in "Transport Processes in Pharmaceutical Systems," Amidon et al., Ed., Marcell Dekker, 185-218, 2000; Balant et al., *Eur. J. Drug Metab. Pharmacokinet.* 1990, 15, 143-53; Balimane and Sinko, *Adv. Drug Delivery Rev.* 1999, 39, 183-209; Browne, *Clin. Neuropharmacol.* 1997, 20, 1-12; Bundgaard, *Arch. Pharm. Chem.* 1979, 86, 1-39; Bundgaard, *Controlled Drug Delivery* 1987, 17, 179-96; Bundgaard, *Adv. Drug Delivery Rev.* 1992, 8, 1-38; Fleisher et al., *Adv. Drug Delivery Rev.* 1996, 19, 115-130; Fleisher et al., *Methods Enzymol.* 1985, 112, 360-381; Farquhar et al., *J. Pharm. Sci.* 1983, 72, 324-325; Freeman et al., *J. Chem. Soc., Chem. Commun.* 1991, 875-877; Friis and Bundgaard, *Eur. J. Pharm. Sci.* 1996, 4, 49-59; Gangwar et al., *Des. Biopharm. Prop. Prodrugs Analogs,* 1977, 409-421; Nathwani and Wood, *Drugs* 1993, 45, 866-94; Sinhababu and Thakker, *Adv. Drug Delivery Rev.* 1996, 19, 241-273; Stella et al., *Drugs* 1985, 29, 455-73; Tan et al., *Adv. Drug Delivery Rev.* 1999, 39, 117-151; Taylor, *Adv. Drug Delivery Rev.* 1996, 19, 131-148; Valentino and Borchardt, *Drug Discovery Today* 1997, 2, 148-155; Wiebe and Knaus, *Adv. Drug Delivery Rev.* 1999, 39, 63-80; and Waller et al., *Br. J. Clin. Pharmac.* 1989, 28, 497-507.

7.4 Methods of Preparation

A DOP-R1 agonist and/or a DOP-R2 antagonist or a pharmaceutically acceptable salt, solvate, hydrate, or prodrug thereof may be prepared by any method known to those of skill in the art.

In one embodiment, for example, TAN-67 may be synthesized as disclosed in Nagase et al. *Jpn. J. Pharmacol.* 1994, 64, suppl. 1, 35; Nagase et al. *Jpn. J. Pharmacol.* 1996, 71, suppl. 9p. TAN-67 may also be obtained from Toray Industries (Kanagawa, Japan). TAN-67 may be dissolved in 0.9% saline shortly before administration.

In one embodiment, for example, NTB may be synthesized as disclosed in Portoghese et al. *Eur. J. Pharmacol.* 1992, 218, 195-196. NTB may also be purchased from Sigma-Aldrich (St. Louis, Mo., USA).

In one embodiment, DPDPE may be purchased from Peninsula Laboratory, Inc. (Belmont, Calif.). In another embodiment, 5'-NTII may be purchased from Sigma-Aldrich (St. Louis, Mo., USA).

In one embodiment, for example, (−)-N-(Cyclopropylmethyl)-4,14-dimethoxymorphinan-6-one (cyprodime) may be synthesized as disclosed in Schmidhammer et al. *J. Med. Chem.* 1989, 32, 418-421.

In one embodiment, clocinnamox may be obtained from J. W. Lewis, Bristol University, Bristol, U.K. In another embodiment, etonitazenyl isothiocyanate may be purchased from Merck Laboratories, Hoffman LaRoche (Nutly, N.J., USA). In another embodiment, β-funaltrexamine (β-FNA) may be purchased from RBI (Natick, Mass., USA). In another embodiment, CTOP, and naloxanazine may be purchased from Sigma-Aldrich (St. Louis, Mo., USA).

The peptides and peptide analogs agonists and antagonists may be prepared using virtually any art-known technique for the preparation of peptides. For example, the peptides may be prepared using conventional step-wise solution or solid phase peptide syntheses, recombinant DNA techniques, or semi-synthetic techniques.

The peptides and peptide analogs agonists and antagonists may be prepared using conventional step-wise solution or solid phase peptide synthesis (see, e.g., Merrifield, R. B., 1963, *J. Am. Chem. Soc.* 85:2149-2154; Chemical Approaches to the Synthesis of Peptides and Proteins, Williams et al., Eds., 1997, CRC Press, Boca Raton Fla., and references cited therein; Solid Phase Peptide Synthesis: A Practical Approach, Atherton & Sheppard, Eds., 1989, IRL Press, Oxford, England, and references cited therein).

Alternatively, the peptides and peptide analogs agonists and antagonists may be prepared by way of segment condensation, as described, for example, in Liu et al., 1996, Tetrahedron Lett. 37(7):933-936; Baca, et al., 1995, *J. Am. Chem. Soc.* 117:1881-1887; Tam et al., 1995, *Int. J. Peptide Protein Res.* 45:209-216; Schnolzer and Kent, 1992, *Science* 256: 221-225; Liu and Tam, 1994, *J. Am. Chem. Soc.* 116(10): 4149-4153; Liu and Tam, 1994, *Proc. Natl. Acad. Sci. USA* 91:6584-6588; Yamashiro and Li, 1988, *Int. J. Peptide Protein Res.* 31:322-334). This is particularly the case with glycine containing peptides. Other methods useful for synthesizing the peptides and peptide analogs agonists and antagonists are described in Nakagawa et al., 1985, *J. Am. Chem. Soc.* 107:7087-7092.

The peptides and peptide analogs agonists and antagonists can be purified by art-known techniques such as reverse phase chromatography high performance liquid chromatography, ion exchange chromatography, gel electrophoresis, affinity chromatography and the like. The actual conditions used to purify a particular peptide will depend, in part, on synthesis strategy and on factors such as net charge, hydrophobicity, hydrophilicity, etc., and will be apparent to those having skill in the art. Multimeric branched peptides can be purified, e.g., by ion exchange or size exclusion chromatography.

For affinity chromatography purification, any antibody which specifically binds the peptide may be used. For the production of antibodies, various host animals, including but not limited to rabbits, mice, rats, etc., may be immunized by injection with a peptide. The peptide may be attached to a suitable carrier, such as BSA, by means of a side chain functional group or linkers attached to a side chain functional group. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacilli Calmette-Guerin) and *Corynebacterium parvum*.

In certain embodiments, DOP-R1 agonists, DOP-R2 antagonists, and MOP-R antagonists for administration may be freshly prepared in steril physiological saline or dissolved in 0.9% NaCl solution containing 0.01% Triton X-100.

7.5 Pharmaceutical Compositions

In one embodiment, DOP-R1 agonist, or a pharmaceutically acceptable salt, solvate, hydrate, or prodrug thereof, can be administered in any form deemed useful by the practitioners of skill in the art. In certain embodiments, DOP-R1 agonist is administered in a pharmaceutical composition comprising one or more pharmaceutically acceptable carriers, excipients or diluents.

In another embodiment, DOP-R2 antagonist, or a pharmaceutically acceptable salt, solvate, hydrate, or prodrug thereof, can be administered in any form deemed useful by the practitioners of skill in the art. In certain embodiments, DOP-R2 antagonist is administered in a pharmaceutical composition comprising one or more pharmaceutically acceptable carriers, excipients or diluents.

In another embodiment, MOP-R antagonist, or a pharmaceutically acceptable salt, solvate, hydrate, or prodrug thereof, can be administered in any form deemed useful by the practitioners of skill in the art. In certain embodiments, MOP-R antagonist is administered in a pharmaceutical composition comprising one or more pharmaceutically acceptable carriers, excipients or diluents.

The DOP-R1 agonists, DOP-R2 antagonists, and MOP-R antagonists may be administered alone, or in combination with one or more DOP-R1 agonists, DOP-R2 antagonists, or MOP-R antagonists, one or more other compounds, or one or more other active ingredients. The pharmaceutical compositions that comprise DOP-R1 agonists, DOP-R2 antagonists, and MOP-R antagonists may be formulated in various dosage forms for oral, parenteral, and topical administration. The pharmaceutical compositions may also be formulated as modified release dosage forms, including delayed-, extended-, prolonged-, sustained-, pulsatile-, controlled-, accelerated- and fast-, targeted-, programmed-release, and gastric retention dosage forms. These dosage forms can be prepared according to conventional methods and techniques known to those skilled in the art (see, Remington: The Science and Practice of Pharmacy, supra; Modified-Release Drug Deliver Technology, Rathbone et al., Eds., Drugs and the Pharmaceutical Science, Marcel Dekker, Inc.: New York, N.Y., 2003; Vol. 126).

In one embodiment provided herein is a pharmaceutical composition comprising a pharmaceutically acceptable carrier and a therapeutically effective amount of one or more DOP-R1 agonists.

In one embodiment provided herein is a pharmaceutical composition comprising a pharmaceutically acceptable carrier and a therapeutically effective amount of one or more DOP-R2 antagonists.

In one embodiment provided herein is a pharmaceutical composition comprising a pharmaceutically acceptable carrier and a therapeutically effective amount of one or more MOP-R antagonists.

In one embodiment provided herein is a pharmaceutical composition comprising a pharmaceutically acceptable carrier and a therapeutically effective amount of one or more DOP-R1 agonists and a therapeutically effective amount of one or more DOP-R2 antagonists.

In one embodiment provided herein is a pharmaceutical composition comprising a pharmaceutically acceptable carrier and a therapeutically effective amount of one or more DOP-R1 agonists and a therapeutically effective amount of one or more MOP-R antagonists.

In one embodiment provided herein is a pharmaceutical composition comprising a pharmaceutically acceptable carrier and a therapeutically effective amount of one or more DOP-R2 antagonists and a therapeutically effective amount of one or more MOP-R antagonists.

In one embodiment provided herein is a pharmaceutical composition comprising a pharmaceutically acceptable carrier and a therapeutically effective amount of one or more DOP-R1 agonists, a therapeutically effective amount of one or more DOP-R2 antagonists, and a therapeutically effective amount of one or more MOP-R antagonists.

In one embodiment provided herein is a pharmaceutical composition comprising a pharmaceutically acceptable carrier and a therapeutically effective amount of TAN-67.

In one embodiment provided herein is a pharmaceutical composition comprising a pharmaceutically acceptable carrier and a therapeutically effective amount of DPDPE.

In one embodiment provided herein is a pharmaceutical composition comprising a pharmaceutically acceptable carrier and a therapeutically effective amount of NTB.

In one embodiment provided herein is a pharmaceutical composition comprising a pharmaceutically acceptable carrier and a therapeutically effective amount of 5'-NTII.

In one embodiment provided herein is a pharmaceutical composition comprising a pharmaceutically acceptable carrier and a therapeutically effective amount of CTOP.

In one embodiment provided herein is a pharmaceutical composition comprising a pharmaceutically acceptable carrier and a therapeutically effective amount of CTAP.

In one embodiment provided herein is a pharmaceutical composition comprising a pharmaceutically acceptable carrier and a therapeutically effective amount of β-FNA.

In one embodiment provided herein is a pharmaceutical composition comprising a pharmaceutically acceptable carrier and a therapeutically effective amount of cyprodime.

In one embodiment provided herein is a pharmaceutical composition comprising a pharmaceutically acceptable carrier and a therapeutically effective amount of TAN-67 and DPDPE.

In one embodiment provided herein is a pharmaceutical composition comprising a pharmaceutically acceptable carrier and a therapeutically effective amount of TAN-67 and 5'-NTII.

In one embodiment provided herein is a pharmaceutical composition comprising a pharmaceutically acceptable carrier and a therapeutically effective amount of TAN-67 and cyprodime.

In one embodiment provided herein is a pharmaceutical composition comprising a pharmaceutically acceptable carrier and a therapeutically effective amount of TAN-67 and CTOP.

In one embodiment provided herein is a pharmaceutical composition comprising a pharmaceutically acceptable carrier and a therapeutically effective amount of TAN-67 and CTAP.

In one embodiment provided herein is a pharmaceutical composition comprising a pharmaceutically acceptable carrier and a therapeutically effective amount of TAN-67 and β-FNA.

In one embodiment provided herein is a pharmaceutical composition comprising a pharmaceutically acceptable carrier and a therapeutically effective amount of DPDPE and NTB.

In one embodiment provided herein is a pharmaceutical composition comprising a pharmaceutically acceptable carrier and a therapeutically effective amount of DPDPE and 5'-NTII.

In one embodiment provided herein is a pharmaceutical composition comprising a pharmaceutically acceptable carrier and a therapeutically effective amount of DPDPE, and cyprodime.

In one embodiment provided herein is a pharmaceutical composition comprising a pharmaceutically acceptable carrier and a therapeutically effective amount of DPDPE, and CTOP.

In one embodiment provided herein is a pharmaceutical composition comprising a pharmaceutically acceptable carrier and a therapeutically effective amount of DPDPE, and CTAP.

In one embodiment provided herein is a pharmaceutical composition comprising a pharmaceutically acceptable carrier and a therapeutically effective amount of DPDPE, and β-FNA.

In one embodiment provided herein is a pharmaceutical composition comprising a pharmaceutically acceptable carrier and a therapeutically effective amount of NTB, and 5'-NTII.

In one embodiment provided herein is a pharmaceutical composition comprising a pharmaceutically acceptable carrier and a therapeutically effective amount of NTB, and cyprodime.

In one embodiment provided herein is a pharmaceutical composition comprising a pharmaceutically acceptable carrier and a therapeutically effective amount of NTB, and CTOP.

In one embodiment provided herein is a pharmaceutical composition comprising a pharmaceutically acceptable carrier and a therapeutically effective amount of NTB, and CTAP.

In one embodiment provided herein is a pharmaceutical composition comprising a pharmaceutically acceptable carrier and a therapeutically effective amount of NTB and β-FNA.

In one embodiment provided herein is a pharmaceutical composition comprising a pharmaceutically acceptable carrier and a therapeutically effective amount of 5'-NTII and cyprodime.

In one embodiment provided herein is a pharmaceutical composition comprising a pharmaceutically acceptable carrier and a therapeutically effective amount of 5'-NTII and CTOP.

In one embodiment provided herein is a pharmaceutical composition comprising a pharmaceutically acceptable carrier and a therapeutically effective amount of 5'-NTII and CTAP.

In one embodiment provided herein is a pharmaceutical composition comprising a pharmaceutically acceptable carrier and a therapeutically effective amount of 5'-NTII and β-FNA.

In one embodiment provided herein is a pharmaceutical composition comprising a pharmaceutically acceptable carrier and a therapeutically effective amount of CTOP and cyprodime.

In one embodiment provided herein is a pharmaceutical composition comprising a pharmaceutically acceptable carrier and a therapeutically effective amount of CTOP and CTAP.

In one embodiment provided herein is a pharmaceutical composition comprising a pharmaceutically acceptable carrier and a therapeutically effective amount of CTOP and β-FNA.

In one embodiment provided herein is a pharmaceutical composition comprising a pharmaceutically acceptable carrier and a therapeutically effective amount of CTAP and cyprodime.

In one embodiment provided herein is a pharmaceutical composition comprising a pharmaceutically acceptable carrier and a therapeutically effective amount of CTAP and β-FNA.

In one embodiment provided herein is a pharmaceutical composition comprising a pharmaceutically acceptable carrier and a therapeutically effective amount of cyprodime and β-FNA.

In one embodiment provided herein is a pharmaceutical composition comprising a pharmaceutically acceptable carrier and a therapeutically effective amount of TAN-67, 5'-NTII, and cyprodime.

In certain embodiments provided herein are pharmaceutical compositions comprising a pharmaceutically acceptable carrier and any combination of therapeutically effective amount of DOP-R1 agonists, DOP-R2 antagonists, and MOP-R antagonists provided herein.

In certain embodiments, DOP-R1 agonists, DOP-R2 antagonists, and MOP-R antagonists useful in the methods are not limited to the ones provided herein.

In one embodiment, the pharmaceutical compositions are provided in a dosage form for oral administration, which comprise DOP-R1 agonists, DOP-R2 antagonists, MOP-R antagonists, or a pharmaceutically acceptable salt, solvate, or prodrug thereof; and one or more pharmaceutically acceptable excipients or carriers.

In certain embodiments, pharmaceutical compositions adapted for oral administration may be provided as capsules or tablets; as powders or granules; as solutions, syrups or suspensions (in aqueous or non-aqueous liquids); as edible foams or whips; or as emulsions. Tablets or hard gelatine capsules may comprise lactose, starch or derivatives thereof, magnesium stearate, sodium saccharine, cellulose, magnesium carbonate, stearic acid or salts thereof. Soft gelatine capsules may comprise vegetable oils, waxes, fats, semisolid, or liquid polyols etc. Solutions and syrups may comprise water, polyols and sugars.

In certain embodiments, the pharmaceutical composition provided herein is provided as a solid dosage form for oral administration.

In certain embodiments, the pharmaceutical composition provided herein is provided as a film-coated tablet.

In certain embodiments, the pharmaceutical composition comprises combination of DOP-R1 agonists, DOP-R2 antagonists, and MOP-R antagonists as the active ingredient.

In certain embodiments, active agents intended for oral administration may be coated with or admixed with a material that delays disintegration and/or absorption of the active agent in the gastrointestinal tract (e.g., glyceryl monostearate or glyceryl distearate may be used). Thus, the sustained release of an active agent may be achieved over many hours and, if necessary, the active agent can be protected from being degraded within the stomach. Pharmaceutical compositions for oral administration may be formulated to facilitate release of an active agent at a particular gastrointestinal location due to specific pH or enzymatic conditions.

In certain embodiments, the formulations are blended together to yield a pharmaceutical composition of the invention. In preferred embodiments, the formulations are provided separately in a pharmaceutical composition of the invention. Useful forms for providing separate formulations of two or more active agents will be apparent to those of skill in the art and include, for example, multilayer tablets, layered capsules, capsules with multiple compartments, mixtures of granulated formulations, coated matrices, coextruded gels or solids, and the like.

In certain embodiments, the combination DOP-R1 agonists, DOP-R2 antagonists, and MOP-R antagonists of this invention may be formulated such that, although the active ingredients are combined in a single dosage unit, the physical contact between the active ingredients is minimized.

In certain embodiments, active agents having different water solubilities, different dosages, or different absorption profiles, can be formulated into a multi-layered tablet. A multi-layered tablet as described herein can provide individual release of each active agent. Furthermore, a multi-layered tablet as described herein, can provide a combination of active agents wherein bioavailability of each active agent is similar to the bioavailability from a separate administration of the active agent. Exemplary multi-layered tablets are described in U.S. Pat. Nos. 6,926,907 and 6,132,768, which are hereby incorporated by reference in their entireties. In the multi-layered tablets, a first formulation can be compressed into one layer, e.g., a core, with a second formulation subsequently added as a second layer, e.g., a coating, of the multilayer tablet. Optionally, one or more subcoats or barrier coats may be added prior to the second layer, see for example U.S. Pat. No. 6,926,907, which is hereby incorporated by reference in its entirety. In certain embodiments, the core comprises the first active agent and the coating comprises the second active agent. In certain embodiments, the coating comprises the first active agent and the core comprises the second active agent. In certain embodiments, one formulation is provided in the core of the multi-layered tablet, and the other formulation is provided in a coating of the multi-layered tablet. In certain embodiments, a pharmaceutically acceptable barrier separates the layers. In certain embodiments, where suitable, the layers are in contact. Methods for making both multilayered and multicoated tablets are described in, e.g., Gunsel, "Compression Coated and Layer Tablets," in *Pharmaceutical Dosage Forms: Tablets, Vol.* 1, Lieberman and Lachman (Eds.), Dekker, N.Y. (1980), which is hereby incorporated by reference in its entirety.

In further embodiments, each formulation can be granulated individually and combined in a granulated pharmaceutical composition. Such a composition can be, for example, compressed into tablets or provided in capsules. In certain embodiments, the granules of one or more of the formulations can be coated. In certain embodiments, the granules of one or more of the formulations can be uncoated.

Granulation is performed in a conventional manner known to the ordinary skilled artisan. Any suitable granulation methods can be used to mix the formulation. In one embodiment, a wet granulation process can be used to mix one or more components of the formulation. For example, high shear granulation or fluid-bed granulation processes can be used. Any suitable commercially available granulation apparatuses can be used in these processes. In another embodiment, a dry granulation process can be used to mix one or more components of the formulation. For example, slugging or roller compaction can be used.

In certain embodiments, multilayer dosage forms may be produced by coextrusion. Typically, coextrusion comprises preparation of two or more molten compositions as described above, and passing these molten compositions into a joint coextrusion die. The shape of the coextrusion die can be selected to match the desired form of the pharmaceutical composition or unit dose form.

In another embodiment, a multi-compartment formulation technology is applied for controlling and extending the release of active agents from a capsule. The multi-compartment formulation means dividing the total dose into several small units (microforms such as microcapsules, pellets and microtablets; small microunits, usually having a size of under 3 mm, obtained by various preparation processes, e.g., coacervation, extrusion, compression, tabletting). Multi-compartment capsules with control release properties as described by Digenis et al., U.S. Pat. No. 5,672,359, and water permeable capsules with a multi-stage drug delivery system as described by Amidon et al., U.S. Pat. No. 5,674,530, may be used to formulate the compositions of the present invention.

In certain embodiments, the parts of the multi-compartment dosage form, e.g., a capsule compartment wall, a solid compartment, or a closure or linker, comprise a pharmaceutically acceptable polymeric blend (and adhesive material if adhesive welds are formed) which is generally regarded as safe, e.g., for oral ingestion and is capable of being formed into the required shape of a capsule compartment wall, a solid compartment, or a closure or linker as described above. A preferred method of forming the polymer material into the desired shape is injection molding, which may be a hot or cold runner injection molding process.

In certain embodiments, the formulations comprise a pharmaceutical dosage form in which a pharmaceutically acceptable polymeric blend is extruded by hot melt into, or is injection molded into multi-compartmental dosage forms. Polymers with desirable physio-chemical characteristics for releasing an active agent, for instance, rapid dissolution, immediate release, delayed release, pulsatile release, or modified release can be used to prepare different compartments of the multi-compartmental dosage form.

In certain embodiments, the pharmaceutical dosage form may comprise a plurality of capsule compartments each bounded and physically separated from at least one adjacent compartment by a wall made of a pharmaceutically acceptable polymer material, such as described herein, wherein one or more of the compartments contain active agents. Adjacent compartments may be connected together in the assembled dosage form and may be retained together by the connection at least prior to administration to a patient. Suitably in the assembled dosage form of this first embodiment there are at least two, for example three, such capsule compartments. Three or more such compartments may be linearly disposed in the assembled dosage form, e.g., in an arrangement comprising two end compartments at opposite ends of the line, and one or more intermediate compartments. Suitably there may be two such capsule compartments. Suitably one of such two capsule compartments may be made of a material which is a sustained release component, i.e., so that the capsule compartment wall dissolves, bursts or is otherwise breached to release its contents after a time delay, e.g., when the compartment has reached the intestine. Suitably the other of such two capsule compartments may be made of a material which is an immediate release component, i.e., so that the capsule compartment wall dissolves, bursts or is otherwise breached to release its contents immediately or effectively immediately, e.g., when the compartment is in the mouth or stomach.

In certain embodiments, one or more, e.g., all of the capsule compartments may for example be substantially cylindrical, which term includes shapes which have a circular, oval or oblate circular cross section across the longitudinal axis, and shapes which have parallel or tapering e.g., with side walls which taper conically over at least part of their extent. Such substantially cylindrical capsule compartments may be provided with connectable parts at one or both of their longitudinally disposed ends so that the assembled dosage form may also be overall of a substantially cylindrical shape.

In certain embodiments, the dimensions and shape of each of the compartments and hence of the overall assembled dosage form may be determined by the nature and quantity of the material to be contained therein and the intended mode of administration and intended recipients. For example a dosage form intended for oral administration may be of a shape and size similar to that of known capsules intended for oral administration.

In certain embodiments, active agents contained in any capsule compartment may be present in any suitable form, e.g., as a powder, granules, compact, microcapsules, gel, syrup or liquid provided that the capsule compartment wall material is sufficiently inert to the liquid content of the latter three forms. The contents of the compartments, e.g., active agents, may be introduced into the compartments by standard methods such as those used conventionally for filling capsules, such as dosating pins or die filling.

In certain embodiments, the compartments may differ from each other in their drug content release characteristics, and this may be achieved in various ways. For example one or more solid and/or capsule compartments may be substantially immediate release, i.e., releasing their drug contents substantially immediately upon ingestion or on reaching the stomach. This may for example be achieved by means of the matrix polymer or the capsule compartment wall dissolving, disintegrating or otherwise being breached to release the drug content substantially immediately.

For example one or more solid and/or capsule compartments may be sustained-release compartments. Preferably these are solid compartments, as a bulk matrix of polymer is likely to dissolve or disperse more slowly to release its drug content that a thin walled capsule.

For example one or more solid and/or capsule compartments may be pulsed-release compartments for example releasing their drug content at a specific predetermined point in a patient's gastro-intestinal system. This may be achieved by the use of polymer materials which dissolve or disperse only at defined pH environments.

For example, one capsule compartment may be effectively immediate release and the other may be sustained, delayed or pulsed release. To achieve this for example one capsule compartment may be made of polymer materials which cause the capsule compartment to release its drug content in the stomach or upper part of the digestive tract, and the linker (acting as a closure for the second compartment) and the second compartment itself may be made of materials, e.g., the above described enteric polymers, which release their drug content only in the intestinal environment.

In certain embodiments, determination of the time or location within the gastro-intestinal tract at which a compartment releases its drug substance content may be achieved by for example the nature of the compartment material, e.g., a solid compartment matrix polymer or a capsule compartment wall material, or in the case of an end compartment which is closed by a closure, by the nature of the closure material. For example the wall of different, e.g., adjacent, compartments may be made of polymers which are different or which otherwise differ in their dissolution or disintegration characteristics so as to endow different compartments with different drug release characteristics. Similarly for example the polymer matrix material of different, e.g., adjacent, solid compartment may be made of polymers which are different or which otherwise differ in their dissolution or disintegration characteristics so as to endow different solid compartments with different drug release characteristics.

For example the matrix, wall or closure material may be a polymer which dissolves or disperses at stomach pH to release the drug substance in the stomach. Alternatively the wall material of different compartments may differ so that different compartments have different release characteristics.

For example a solid or a capsule compartment may have respectively a matrix or a wall or a closure comprising an enteric polymer which dissolves or disperses at the pH of the small or large intestine to release the drug substance in the intestine.

Additionally or alternatively, the wall material may differ in thickness between compartments so that thicker walled compartments disrupt more slowly than thinner walled compartments.

Additionally or alternatively, the compartment walls or the closure may have areas or points of weakness which preferentially dissolve and may thereby determine the time of onset and/or rate of release of the drug substance content. For example such points of weakness may comprise holes, e.g., small holes, e.g., laser-drilled holes in the compartment wall or the closure, these holes being closed and/or covered with a film of a polymer material that dissolves at a predetermined point in the digestive tract, for example an enteric polymer material. For example such points of weakness may comprise thinned parts in a capsule compartment wall formed during the molding operation in which the capsule compartment is formed.

In certain embodiments, the compartments may additionally or alternatively have surface or other constructional features that modify their drug release characteristics. For example solid compartments may be provided with internal cavities or channels to create a large surface area. For example solid compartments may be in the form of hollow cylinders, donuts, or toroids, which shapes are known to tend towards first-order dissolution or erosion in liquid media and correspondingly to tend toward first-order release of drug content dispersed therein.

In another embodiment, the pharmaceutical compositions are provided in a dosage form for parenteral administration, which comprise a compound provided herein or a pharmaceutically acceptable salt, solvate, or prodrug thereof; and one or more pharmaceutically acceptable excipients or carriers.

Pharmaceutical compositions adapted for parenteral administration include aqueous and non-aqueous sterile injectable solutions or suspensions, which may contain antioxidants, buffers, bacteriostats and solutes that render the compositions substantially isotonic with the blood of an intended recipient. Other components that may be present in such compositions include water, alcohols, polyols, glycerine and vegetable oils, for example. Compositions adapted for parenteral administration may be presented in unit-dose or multi-dose containers, for example sealed ampules and vials, and may be stored in a freeze-dried (lyophilized) condition requiring only the addition of a sterile liquid carrier, e.g., sterile saline solution for injections, immediately prior to use. Extemporaneous injection solutions and suspensions may be prepared from sterile powders, granules and tablets. In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water-free concentrate in a hermetically-sealed container such as an ampule or sachette indicating the quantity of active agent. Where the composition is to be administered by infusion, it can be dispensed with an infusion bottle containing sterile pharmaceutical grade water or saline. Where the composition is administered by injection, an ampule of sterile saline can be provided so that the ingredients may be mixed prior to administration.

In another embodiment, a combination of DOP-R1 agonists, DOP-R2 antagonists, and MOP-R antagonists can be delivered in a controlled-release system. For example, a combination of DOP-R1 agonists, DOP-R2 antagonists, and MOP-R antagonists may be administered using intravenous infusion, an implantable osmotic pump, a transdermal patch, liposomes, or other modes of administration. In one embodiment, a pump may be used (see Langer, supra; Sefton, 1987, CRC Crit. Ref. Biomed. Eng. 14:201; Buchwald et al, 1980, Surgery 88:507; Saudek et al, 1989, *N. Engl. J. Med.* 321: 574). In another embodiment, the compound can be delivered in a vesicle, in particular a liposome (see Langer, *Science* 249:1527-1533 (1990); Treat et al, in Liposomes in the Therapy of Infectious Disease and Cancer, Lopez-Berestein and Fidler (eds.), Liss, New York, pp. 353-365 (1989); WO 91/04014; U.S. Pat. No. 4,704,355; Lopez-Berestein, ibid., pp. 317-327; see generally ibid.). In another embodiment, polymeric materials can be used (see Medical Applications of Controlled Release, Langer and Wise (eds.), CRC Press: Boca Raton, Fla., 1974; Controlled Drug Bioavailability, Drug Product Design and Performance, Smolen and Ball (eds.), Wiley: New York (1984); Ranger and Peppas, *J. Macromol. Sci. Rev. Macromol. Chem.* 23:61, 1953; see also Levy et al, 1985, *Science* 228:190; During et al, 1989, Ann Neurol. 25:351; Howard et al, 1989, *J. Neurosurg.* 71:105.

In yet another embodiment, the pharmaceutical compositions are provided in a dosage form for topical administration, which comprise a compound provided herein or a pharmaceutically acceptable salt, solvate, or prodrug thereof; and one or more pharmaceutically acceptable excipients or carriers.

In another embodiment, pharmaceutical compositions adapted for transdermal administration may be provided as discrete patches intended to remain in intimate contact with the epidermis of the recipient for a prolonged period of time. Pharmaceutical compositions adapted for topical administration may be provided as ointments, creams, suspensions, lotions, powders, solutions, pastes, gels, sprays, aerosols or oils. For topical administration to the skin, mouth, eye or other external tissues a topical ointment or cream is preferably used. When formulated in an ointment, the active ingredient may be employed with either a paraffinic or a water-miscible ointment base. Alternatively, the active ingredient may be formulated in a cream with an oil-in-water base or a water-in-oil base. Pharmaceutical compositions adapted for topical administration to the eye include eye drops. In these compositions, the active ingredient can be dissolved or suspended in a suitable carrier, e.g., in an aqueous solvent. Pharmaceutical compositions adapted for topical administration in the mouth include lozenges, pastilles and mouthwashes.

In another embodiment, pharmaceutical compositions adapted for nasal and pulmonary administration may comprise solid carriers such as powders (preferably having a particle size in the range of 20 to 500 microns). Powders can be administered in the manner in which snuff is taken, i.e., by rapid inhalation through the nose from a container of powder held close to the nose. Alternatively, compositions adopted for nasal administration may comprise liquid carriers, e.g., nasal sprays or nasal drops. Alternatively, inhalation of compounds directly into the lungs may be accomplished by inhalation deeply or installation through a mouthpiece into the oropharynx. These compositions may comprise aqueous or oil solutions of the active ingredient. Compositions for administration by inhalation may be supplied in specially adapted devices including, but not limited to, pressurized aerosols, nebulizers or insufflators, which can be constructed so as to provide predetermined dosages of the active ingredient. In a preferred embodiment, pharmaceutical compositions of the invention are administered into the nasal cavity directly or into the lungs via the nasal cavity or oropharynx.

The pharmaceutical compositions provided herein may be provided in unit-dosage forms or multiple-dosage forms. Unit-dosage forms, as used herein, refer to physically discrete units suitable for administration to human and animal subjects and packaged individually as is known in the art. Each unit-dose contains a predetermined quantity of the active ingredient(s) sufficient to produce the desired therapeutic effect, in association with the required pharmaceutical carriers or excipients. Examples of unit-dosage forms include ampoules, syringes, and individually packaged tablets and capsules. Unit-dosage forms may be administered in fractions or multiples thereof. A multiple-dosage form is a plurality of identical unit-dosage forms packaged in a single container to be administered in segregated unit-dosage form. Examples of multiple-dosage forms include vials, bottles of tablets or capsules, or bottles of pints or gallons.

The pharmaceutical compositions provided herein may be administered at once, or multiple times at intervals of time. It is understood that the precise dosage and duration of treatment may vary with the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the formulations.

In certain embodiments the pharmaceutical composition comprises the following inactive ingredients: lactose monohydrate, hypromellose, hydroxypropyl cellulose, magnesium stearate, microcrystalline cellulose, sodium starch glycolate, sodium lauryl sulfate and titanium dioxide and trace amounts of color additives, including FD&C Yellow #6.

In certain embodiments, pharmaceutical kits useful for the treatment of alcoholism and alcohol dependence, which comprise a therapeutically effective amount of (i) at least one delta opioid receptor-1 agonist and (2) at least one delta opioid receptor-2 antagonist, in one or more containers, are also within the ambit of the present invention. Sterilization of the container may be carried out using conventional sterilization methodology well known to those skilled in the art. Component (i), and component (ii) may be in the same container or in separate containers. The containers of materials may comprise separate containers, or one or more multi-part containers, as desired. Component (i), and component (ii), may be separate, or physically combined into a single dosage form or unit as described above. Such kits may further include, if desired, one or more of various conventional pharmaceutical kit components, such as for example, one or more pharmaceutically acceptable carriers, additional vials for mixing the components, etc., as will be readily apparent to those skilled in the art. Instructions, either as inserts or as labels, indicating quantities of the components to be administered, guidelines for administration, and/or guidelines for mixing the components, may also be included in the kit.

7.6 Effective Dosage

Selection of the preferred effective dose will be readily determinable by a skilled artisan based upon considering several factors, which will be known to one of ordinary skill in the art. Such factors include the particular form of DOP-R1 agonists, DOP-R2 antagonists, and MOP-R antagonists, and their pharmacokinetic parameters such as bioavailability, metabolism, half-life, etc., which will have been established during the usual development procedures typically employed in obtaining regulatory approval for a pharmaceutical compound. Further factors in considering the dose include the condition or disease to be treated or the benefit to be achieved in a normal individual, the body mass of the patient, the route of administration, whether administration is acute or chronic, concomitant medications, and other factors well known to affect the efficacy of administered pharmaceutical agents. Thus the precise dosage should be decided according to the judgment of the practitioner and each patient's circumstances, e.g., depending upon the condition and the immune status of the individual patient, and according to standard clinical techniques.

In one embodiment, a combination of DOP-R1 agonists, DOP-R2 antagonists, and/or MOP-R antagonists is administered to a subject suffering from a substance-related disorder in a dosage range of 0.1 to 300 mg per day.

In one embodiment, a combination of DOP-R1 agonists, DOP-R2 antagonists, and/or MOP-R antagonists is administered to a subject suffering from a substance-related disorder in a dosage range of 0.1 to 150 mg per day.

In one embodiment, a combination of DOP-R1 agonists, DOP-R2 antagonists, and/or MOP-R antagonists is administered to a subject suffering from a substance-related disorder in a dosage range of 0.1 to 50 mg per day.

In one embodiment, a combination of DOP-R1 agonists, DOP-R2 antagonists, and/or MOP-R antagonists is administered to a subject suffering from a substance-related disorder in a dosage range of 0.1 to 20 mg per day.

For use in the treatment of diseases characterized by abnormally high consumption of alcohol, by way of general guidance, a daily oral dosage of active ingredient(s) can be about 0.001 to 1000 mg/kg of body weight. Ordinarily a dose of 0.1 to 500 mg/kg per day in divided doses one to four times a day or in sustained release form is effective to obtain the desired results.

In one embodiment, when one or more DOP-R1 agonists, DOP-R2 antagonists, and MOP-R antagonists are administered in combination, the dosage amount of each component may be reduced by about 50-80% relative to the usual dosage of the component when it is administered alone as a single agent for treatment of substance abuse and dependence, in view of the synergistic effect of the combination.

8. EXAMPLES

8.1 Example 1

The DOP-R2 Antagonist Naltriben (NTB) Dose Dependently Decreases Ethanol Consumption in C57BL/6 Mice The present example demonstrates the effect of the DOP-R2 selective antagonist naltriben (NTB) and the non selective ligands naltrexone (NTX) and naltrindole (NTI) on ethanol consumption and preference in C57BL/6 mice.

Material and Methods

Animals and Housing.

Male C57BL/6 mice (20-23 g, Taconic) were individually housed in ventilated PLEXIGLAS® cages at ambient temperature (21° C.) in a room maintained on a reversed 12L:12D cycle (lights off at 10.00, lights on at 22.00). Food and water was provided ad libitum. The mice were given time to acclimatize to the individual housing conditions and reverse light cycle before the start of the experiments. Mice were weighed weekly. All procedures were pre-approved by the Gallo Center Institutional Animal Care and Use Committee and were in accordance with National Institutes of Health Guide for the Care and Use of Laboratory Animal.

Limited Access Drinking Paradigm.

From Monday through Friday, mice were presented with a 2-bottle choice (water or 10% ethanol) for a 4 hour period (11.00-15.00) while in the dark cycle. Outside the 2-bottle choice period, all mice had unlimited access to water. All fluids were presented in 100-ml graduated glass cylinders with stainless-steel drinking spouts inserted through two grommets in front of the cage. Bottles were weighed to the nearest decigram (0.1 g) at the start and end of the 2-bottle choice period. The positions of the tubes containing water and ethanol were reversed daily to limit the effects of positional preference. Mice (9 per group) were injected with drugs subcutaneously (s.c.) on Friday 30 minutes before the start of the 2-bottle choice period.

Drugs.

Ethanol and sucrose solutions were prepared in tap water using 95% (vol/vol) ethanol (Gold Shield Chemical Co., Hayward, Calif., USA). Naltriben mesylate (NTB), 7-benzylidenenaltrexone maleate (BNTX) were purchased from Tocris (MO, USA). TAN-67 dihydrobromide, naltrindole hydrochloride (NTI) and naltrexone hydrochloride (NTX) were from Sigma-Aldrich (MO, USA). All compounds were dissolved in saline, with the exception of BNTX and NTB, which were dissolved in 5% DMSO. All drugs were made up immediately prior to injection and were administered s.c. at a volume of 10 ml/kg.

Data Analysis.

Baseline values were determined by taking the average of the consumption over the three days prior to injection. Statistical analysis was performed using Prism software (GraphPad, San Diego, Calif.). Significance was determined by means of one-way ANOVA or two-way ANOVA (repeated measures). A post-hoc Newman-Keuls (one-way ANOVA) or Bonferroni (two-way ANOVA) test was used when a significant overall effect was found ($p<0.05$). (*, $p<0.05$; , $p<0.01$; *, $p<0.001$).

Results

Two groups of 9 male C57BL/6 mice were conditioned to prefer a 10% ethanol solution over water in a limited access drinking paradigm (see methods). After 15 training sessions (3 weeks), mice showed a stable 75% preference for ethanol over water.

Whereas a dose of 1.5 mg/kg of the non-selective opioid antagonist NTX resulted in a decrease in ethanol consumption [$F(3,40)=13.39$, $p<0.0001$], a relatively high dose (5 mg/kg), which likely antagonizes both MOP-Rs and DOP-Rs, had only moderate effects on the drinking behavior of the mice (FIG. 1B). The non-selective DOP-R antagonist NTI (10 or 15 mg/kg) did not alter either ethanol consumption or preference [$F(3,40)=1.89$, $p=0.13$] (FIG. 1A). In contrast, the DOP-R2-selective antagonist NTB, dose dependently decreased both ethanol consumption [$F(3,32)=8.06$, $p=0.0004$] and ethanol preference [$F3,32)=3.476$, $p=0.027$] in C57BL/6 mice (FIG. 1B), consistent with the effects of this drug previously reported for rats (Krishnan Sarin et al., *Pharmacol Biochem Behav.* 1995, 52:153-59).

8.2 Example 2

The DOP-R1 Agonist TAN-67 Decreases Ethanol Consumption in C57BL/6 Mice

The present example demonstrates the effect of TAN-67 on ethanol consumption in C57BL/6 mice.

For materials and methods please refer to Example 1.

Results

Since the DOP-R2-selective antagonist NTB but not the DOP-R1/R2 selective antagonist NTI decreased ethanol consumption, antagonism of DOP-R1 with NTI could be opposing the effects of NTI at DOP-R2. To examine this possibility, the effect of the DOP-R1-selective antagonist BNTX and the DOP-R1-selective agonist TAN-67 on ethanol consumption was tested. BNTX (10 mg/kg) did not affect ethanol consumption (FIG. 2), unlike the DOP-R2-selective antagonist NTB (FIG. 1). In contrast, administration of the DOP-R1 agonist TAN-67 showed a dose-dependent decrease in ethanol consumption and preference (FIG. 2). This effect was blocked by the DOP-R1 antagonist BNTX (25 mg/kg, FIG. 2).

8.3 Example 3

TAN-67 Decreases Ethanol Consumption by Activation of DOP-R1, NTB Decreases Ethanol Consumption by Inhibition of DOP-R2

The present example demonstrates the effect of TAN-67 and NTB on ethanol consumption in C57BL/6 mice.

For materials and methods please refer to Example 1.

Results

Because the DOP-R1 and DOP-R2 are defined solely by pharmacology, whether the DOP-R1 agonist TAN-67 and the DOP-R2 antagonist NTB decrease ethanol consumption by acting on different receptor sites was tested. Co-administration of DOP-R1 agonist TAN-67 (25 mg/kg) together with the DOP-R2 antagonist NTB (10 mg/kg) caused a greater decrease in drinking than either drug alone (FIG. 3A). Furthermore, co-administration of low amounts of NTB (5 mg/kg) and TAN-67 (12.5 mg/kg), that by themselves have no effect on ethanol consumption, caused a significant decrease in ethanol consumption (FIG. 3B).

8.4 Example 4

TAN-67 Decreases Ethanol Consumption without being Rewarding by Itself

The present example demonstrates that TAN-67 is not rewarding at a therapeutically effective dose.

Material and Methods

8.5 Example 5

Neither the DOP-R1 Agonist TAN-67 nor the DOP-R2 Antagonist NTB Affect General Locomotion or Natural Reward, as Determined by Sucrose Consumption The present example demonstrates that the effects of the DOP-R1 agonist TAN-67 and the DOP-R2 antagonist NTB are not caused by changes in general locomotor activity or natural reward.

Material and Methods

To determine the effect of DOP-R subtype-selective drugs on mouse locomotion, the following locomotor activity assay was performed. On the testing day, mice (n=8) were habituated to the locomotor boxes for 30 minutes prior to the behavioral assay. Mice were injected s.c. with vehicle (saline or 5% DMSO), 25 mg/kg TAN-67 or 6 mg/kg NTB and placed back in the locomotor boxes. Locomotor activity was assayed 30 minutes after injection for 4 hours using Accuscan Digipro activity monitors (Accuscan, Columbus, Ohio). All mice were tested during their light phase between the hours of 9.00 and 14.00. Mice were placed into custom-made acrylic boxes that were 21×21 cm and 28 cm tall. One acrylic box was used per single Accuscan monitor (Accuscan). Activity monitors were themselves housed inside sound-attenuating chambers (Med-Associates, St Albans, Vt.) equipped with lights and fans, both of which were turned on during the testing session. To eliminate variability due to handling and novelty, on the two days before the testing day, mice were habituated to the locomotor boxes for 30 minutes injected with saline and placed in the locomotor box for an additional 30 minutes.

Results

It is possible that the effects of TAN-67 and NTB on ethanol consumption are secondary to the effects on locomotion. However, mice injected with 25 mg/kg TAN-67 or 6 mg/kg NTB did not show any significant difference in locomotor activity compared to vehicle treated animals [F(3,28)=1.15, p=0.34], suggesting this is not the case (FIG. 4A). In addition, neither TAN-67 [F(1,16)=0.057, p=0.81] nor NTB [F(1,16)= 0.62, p=0.44] had an affect on sucrose intake, demonstrating that the effect on consumption was selective to ethanol but not sucrose, a "natural" reward (FIG. 4B).

8.6 Example 6

DOP-R1 Activation in the Ventral Tegmental Area (VTA) Attenuates Ethanol Consumption while TIPP-psi, a DOP-R Selective Antagonist, Makes Low Drinkers Drink More The ventral tegmental area (VTA) is a key brain region in the reinforcement circuit that is implicated in addiction and alcoholism. Supporting data from this brain region were collected.

Material and Methods

Animals.

Male Lewis rats (Harlan Laboratories, Indianapolis, Ind.) weighing between 275-300 g were individually housed in a temperature controlled colony room (21° C.) maintained on a reversed light/dark cycle 12L:12D cycle (lights off at 10 A.M., lights on at 10 P.M.). All experiments were performed during the dark portion of the cycle. Food and water was provided ad libitum.

Ethanol Self-Administration.

Ethanol was administered via a two-bottle continuous access, free-choice paradigm in which one bottle contained 10% ETOH (v/v) and the other bottle contained water. Sucrose was never added to the ethanol solution. The amount of ETOH and water consumed was measured at the same time daily (10 A.M.). Stable self-administration (<15% change in drinking over 3 consecutive days) was achieved in 12-14 weeks. Experiments began after a stable level of ethanol self-administration was achieved for all animals. Animals were weighed daily. Bottles were identical and their positions were counterbalanced and rotated daily. Change in drinking was calculated by subtracting the amount of drinking (mg/kg) on the day following treatment from the amount of drinking (mg/kg) on the day prior to treatment.

VTA Cannulations.

Animals were anesthetized and maintained on isoflurane (0.5 l/min) as needed for the duration of surgery. Animals were placed in a stereotaxic frame and were implanted with bilateral 26-gauge stainless steel chronic guide cannulas (Plastincs One, Roanoke, Va.) into the VTA (AP, −5.8; ML, ±0.5; DV, −7.0) based on the atlas of Paxinos and Watson (1997, The rat brain in sterotaxic coordinates, compact, Ed 3. San Diego: Academic). Cannulas were secured to the skull with dental cement. At the end of the surgical procedure, animals were treated with penicillin and topical antibiotics. A stainless steel dummy cannula (Plastics One) was inserted into each guide cannula and remained in place when the guide cannulas were not in use. Animals were allowed a 1 week recovery period before behavioral testing.

VTA Microinjections.

Each injection was made using a 1 µl syringe (Hamilton, Reno, Nev.) attached to 20 cm of PE 50 tubing connected to a 33-gauge injection cannula (Plastics One). Microinjections of 0.5 µl volumes were given at a rate of 0.5 µl/min using a syringe pump (kd Scientific, Hollister, Mass.) into each side of the VTA, except for bicuculline injections, where 0.25 µl was injected per side. Injection cannulas extended 2 mm beyond guide cannulas and were left in place for 1 min following microinjections to minimize the backflow of drug solution. In addition to drug microinjections, physiological saline microinjections were made in every rat to measure the effect of the injection manipulation alone on drinking Drug injections were randomized and counterbalanced. Change in drinking due to drug microinjections was calculated by comparing both the previous day's consumption ("baseline") and to saline injection. At the conclusion of the experiment, animals were anesthetized with pentobarbital and perfused intracardially through the ascending aorta with 0.1 M phosphate buffered saline followed by 10% formalin. Brains were sectioned coronally at 50 µm, mounted and stained with cresyl violet. Only animals with confirmed injection sites within the VTA were included. No behavioral differences were observed between animals with anterior compared with posterior cannula placements.

Drugs and Doses.

For behavioral experiments, DPDPE (10mM; Sigma, St. Louis, Mo.), TIPP-ψ (5 µM; NIDA, Bethesda, Md.), Bicuculline (1 mM; Sigma), DAMGO (0.2 mM; Sigma), and CTOP (10 mM; Tocris, Ellisville, Mo.) were prepared in physiological saline for microinjection into the VTA. For electrophysiology, all drugs were applied by bath perfusion. Stock solutions were made and diluted in artificial CSF immediately before application. All chemicals were obtained from Sigma or Tocris except TIPP-ψ, which was acquired from NIDA.

Data Analysis.

Results are presented as mean±SEM where appropriate. For behavioral data, drinking was analyzed using 24 h time points. Raw drinking data were used for paired Student's t test comparisons probing drug effects on drinking compared with baseline or saline injections, a more conservative comparison than analyzing normalized data. Drinking comparisons and regression analyses were completed in Excel (v.11.4.1; Microsoft). Because TIPP-ψ induced a long-lasting, robust increase in EtOH consumption in low-drinking animals (see below), cross-over saline data could not be obtained for three animals that received the TIPP-ψ injection before saline. Baseline data were substituted for these three animals for benefit of statistical comparison. For electrophysiology, the analyzed data were composed of the 4 min of baseline just preceding drug application and minutes 4-7 of drug application. Comparisons across electrophysiology groups were made with one-way ANOVA followed by the Student-Newman-Keuls (SNK) method for multiple comparisons where appropriate using SigmaStat software (SPSS). $p<0.05$ was required for significance in all experiments.

Results

The DOP-R1 selective agonist DPDPE (10 mM) microinjected into the VTA decreased drinking across all animals compared with drinking the day before treatment (n=15, t=2.14, p=0.008) (FIG. 5A). This effect was also evident compared with control saline microinjections in the same rats, and was particularly prominent in low drinkers (n=7, t=2.45, p=0.02) (FIG. 5B). This DPDPE effect on drinking was only at trend level in high drinkers (n=8, t=2.36, p=0.059) (FIG. 5B). Additionally, there was an inverse correlation between baseline EtOH consumption and % baseline drinking following DPDPE administration (n=15, F=6.35, r=0.57, p=0.02), which demonstrated that the lowest drinking animals were the most affected by DPDPE. Consistent with this result, the DOP-R selective antagonist TIPP-ψ (5 µM) microinjected into the VTA increased drinking across all animals compared with EtOH consumption the day preceding treatment (n=14, t=2.16, p=0.006) (FIGS. 5C, E). This was also the case compared with saline injections, and a median split of the data revealed that this effect was again driven by the low drinkers (n=7, t=2.45, p=0.0002 for low drinkers vs n=7, t=2.45, p=0.32 for high drinkers) (FIG. 5D). These data suggest that DOP-R activation by endogenous opioids released in the VTA normally suppresses EtOH intake. Moreover, some animals appear to lack this protective mechanism, resulting in increased EtOH intake.

8.7 Example 7

DPDPE, a DOP-R1 Selective Agonist, Decreases GABA Release in the VTA of Low Drinkers, but not High Drinkers Material and Methods Slice Preparation and Electrophysiology.

Lewis rats were maintained on 2 bottle choice, as described for the behavioral experiments, until their drinking stabilized. Electrophysiological experiments were completed blind to EtOH consumption levels. Recordings were made throughout the VTA. To commence electrophysiological experiments, rats were anesthetized with isoflurane and their brains were removed. Horizontal brain slices (200 µm thick) containing the VTA were prepared using a vibratome (Leica Microsystems, Bannockburn, Ill.). Slices were submerged in artificial CSF solution containing (in mM): 126 NaCl, 1.2 MgCl, 1.4 $NaH_2PO_4$, 2.5 $CaCl_2$, 25 $NaHCO_3$, and 11 glucose saturated with 95% $O_2$-5% $CO_2$ and allowed to recover at 32° C. for at least 1 h. Individual slices were visualized using a Zeiss Axioskop microscope with differential interference contrast optics and infrared illumination. Whole-cell patch-clamp recordings were made at 32° C. using 2.5-5 MΩ pipettes containing (in mM) 128 KCl, 20 NaCl, 1 $MgCl_2$, 1 EGTA, 0.3 $CaCl_2$, 10 HEPES, 2 MgATP, and 0.3 $Na_3GTP$ (pH 7.2, osmolarity adjusted to 275), plus 0.1% biocytin or Lucifer yellow to label the recorded neuron. Signals were amplified using a Multiclamp 700B amplifier (Axon Instruments, Sunnyvale, Calif.), filtered at 2 kHz, and collected at 5 kHz using IGOR Pro (Wavemetric, Portland, Oreg.). Ih was measured by voltage clamping cells and stepping from −60 to −40, −50, −70, −80, −90, −100, and −120 mV. Cells were recorded in voltage-clamp mode (V=−70 mV). Series resistance and input resistance were sampled throughout the experiment with 4 mV, 200 ms hyperpolarizing steps. $GABA_A$ IPSCs were pharmacologically isolated with 6,7-dinitroquinoxaline-2,3(1H,4H)-dione (DNQX: 10 µM), strychnine (1 µM), and sulpiride (10 µM). Picrotoxin (100 µM) was added at the end of some recordings to confirm the remaining signal was due to $GABA_A$ receptor activation. Stimulating electrodes were placed 80-250 µm away from the soma. To measure drug effects on evoked IPSCs, paired pulses (50-ms interval) were delivered once every 10 s. The IPSC amplitude was calculated by comparing a 2 ms period around the peak to a 2 ms interval just before stimulation. The paired-pulse ratio (PPR) was calculated by dividing the amplitude of the second IPSC by that of the first, after averaging together 8 consecutive trials. Spontaneous events were detected by searching the smoothed first derivative of the data trace for values that exceeded a set threshold, and these events were confirmed visually. Dose-response experiments were completed in the presence of a MOP-R antagonist (1 µM CTAP) to insure the observed effect remained DOP-R selective at the 10 µM dose of DPDPE. All neurons were identified as $I_h(+)$ or $I_h(-)$. Wherever possible, Ih(+) neurons were immunocytochemically processed for tyrosine hydroxylase (TH) content as a marker for DA neurons. However, since no results differed across any of these cell groups, the data were grouped together for analysis.

Immunocytochemistry.

Immediately after electrophysiological recording, slices were fixed in 4% formaldehyde for 2 h and then stored at 4° C. in PBS. Slices were preblocked for 2 h in PBS plus 0.3% (v/v) Tween, 0.2% BSA and 5% normal goat serum and then incubated at 4° C. with a rabbit anti-tyrosine hydroxylase polyclonal antibody (1:100). The slices were then washed thoroughly in PBS with 0.3% Tween and 0.2% (w/v) BSA before being agitated overnight at 4° C. with Cy5 or FITC anti-rabbit secondary antibody (1:100). For cells filled with biocytin, fluorescein (DTAF)-conjugated streptavidin (3.25 μl/ml) was also added during this step. Sections were rinsed and mounted on slides using Bio-Rad Fluoroguard Antifade Reagent mounting media (Bio-Rad Laboratories, Hercules, Calif.) and visualized under a Zeiss LSM 510 META microscope. Primary antibodies were obtained from Chemicon International (Billerica, Mass.), secondary antibodies from Jackson ImmunoResearch Laboratories (West Grove, Pa.), and all other reagents from Sigma Chemical (St. Louis, Mo.).

For additional materials and methods please refer to Example 6.

Results

DPDPE (1 μM) significantly inhibited both evoked (FIG. 6) and spontaneous (FIG. 11)) IPSCs in VTA neurons from drinking animals. In contrast, in age-matched, ethanol-naive, control animals there was no effect of DPDPE on $GABA_A$ IPSCs (FIGS. 6A, C, D, 9D, E). The DPDPE effect in drinking animals was blocked by the DOP-R selective antagonist TIPP-ψ (1 μM), indicating that the agonist was acting through the DOP-R (FIG. 6C). Application of the antagonist alone had no effect on either evoked IPSC amplitude (6.8±9.0% decrease from baseline, n=3) or spontaneous IPSCs (8.6±2.4% decrease in frequency and 2.6±1.6% decrease in amplitude, n=2), suggesting that there is no tonic activation of DOP-R in this slice preparation. Importantly, for both evoked IPSCs and spontaneous IPSCs there was an inverse correlation between DPDPE induced inhibition and amount of EtOH consumed, and this relationship was particularly strong for spontaneous IPSC frequency (FIG. 7). Dose-response data were collected to probe whether elevated EtOH consumption shifted the $IC_{50}$ of this DOP-R-mediated effect or whether the maximal effect was smaller in high-drinking and EtOH naive animals. In the animal groups 1 DPDPE was a saturating dose with no apparent shift in the $IC_{50}$ between groups (FIG. 6D).

8.8 Example 8

DOP-R Mediates Ethanol Consumption through $GABA_A$ Signaling

For materials and methods please refer to Example 6.

Results

If presynaptic inhibition of GABA release plays a role in our observed intra-VTA DOP-R modulation of EtOH consumption, then the TIPP-ψ induced increase in drinking should be blocked by coinjection of a $GABA_A$ receptor antagonist. In fact, when the $GABA_A$ receptor antagonist bicuculline (1 mM) was coinjected with TIPP-ψ (5 μM) into the VTA, it completely blocked the TIPP-ψ induced increase in EtOH consumption in low-drinking animals (FIG. 8). Bicuculline also produced a small overall decrease in drinking across all animals following coadministration (n=15, p=0.035). However, a median split revealed that this effect was carried by high-drinking animals (n=7, t=2.45, p=0.017) (FIG. 8) in whom TIPP-ψ alone had no significant effect. Furthermore, TIPP-ψ and bicuculline cotreatment had no effect on EtOH consumption in low-drinking animals (n=8, t=2.36, p=0.79) (FIG. 8). Therefore, VTA GABA neurotransmission plays a critical role in DOP-R mediated control of EtOH consumption in low-drinking animals.

8.9 Example 9

CTOP, a MOP-R Selective Antagonist, Injected in the VTA Decreases Drinking in all Animals while DAMGO, a MOP-R Selective Agonist, Injected in the VTA does not Change Drinking For materials and methods please refer to Example 6.

Results

Microinjection of the MOP-R agonist DAMGO (0.2 mM) into the VTA did not affect drinking (FIG. 9A, C). However, the MOP-R selective antagonist CTOP (10 mM) significantly decreased drinking (FIG. 9B, D). In contrast to the DOP-R antagonist mediated enhancement of ethanol consumption in low drinkers, this MOP-R antagonist mediated decrease was similar in high- and low drinking animals.

8.10 Example 10

Chronically Drinking Rats Decrease their Drinking after Systemic Administration of the Mu Opioid Antagonist Beta-FNA For materials and methods please refer to Example 6.

Results

Chronically drinking rats decrease their drinking after systemic administration of the mu opioid antagonist beta-FNA (FIG. 10).

8.11 Example 11

DPDPE Continues to Inhibit GABA Release in the VTA in Abstinent Animals

For materials and methods please refer to Examples 6 and 7.

Results

After at least 2 months of ethanol consumption, rats were forced to abstain from drinking when the experimenters removed the ethanol-containing solution from their cages. DPDPE effects on GABA release at 3 and 7 days off bottles were tested. At both time points DPDPE maintained its ability to inhibit GABA release onto VTA neurons (FIG. 11).

8.12 Example 12

Repeated Morphine Administration Leads to DOR1-Mediated Inhibition of GABA Release in the VTA Material and Methods Materials and Methods: Male Lewis rats (250-300 g) were housed as in Example 8. In the first part of the experiment, rats received once daily injections of 0.5 mg/kg morphine for 20 days, after which they were sacrificed and the VTA tissue was examined for DOR expression. Standard immunocytochemical methods were used with a DOR-targeted antibody (SC9111) purchased from Santa Cruz Biotechnology, Inc.

For electrophysiology experiments, rats received twice daily injections, 10 hours apart, of 5 mg/kg morphine IP for 7 days. On the 8$^{th}$ day, they received a single injection just prior to sacrificing the animals for slice electrophysiology completed as in Example 7.

Results

Immunocytochemistry indicates that DOR expression increases in the VTA following both chronic drinking and chronic morphine treatment (FIG. 12). Electrophysiological measurements made in VTA neurons show that in morphine-treated animals, as in drinking animals, activating DOR1 inhibits electrically evoked GABA release (FIG. 12).

Example 13

DOPR-1 Agonists Attenuates Cocaine Self Administration

Materials and Methods

Lewis rats (Charles River, Mass.) weighing 275-350 g at the beginning of behavioral testing are housed and treated as previously described. Prior to cocaine self administration, rats are anesthetized with a ketamine-xylazine-acepromazine mixture and implanted with a chronic jugular catheter using methods previously described (Caine & Koob, 1993). Following surgery, rats receive daily administration of the antibiotic ticarcillin (20 mg/day at 100 mg/ml; GlaxoSmithKline, Research Triangle Park, NC). Catheter patency is tested by infusion of the fast-acting barbiturate Brevital (methohexital sodium; 1 mg/0.1 ml; Lilly, Indianapolis, Ind.). Self-administration training is conducted in operant-conditioning chambers enclosed within sound-attenuating cabinets (MED Associates, St. Albans, Vt.). Each chamber contains an active and inactive lever as well as a food dispenser and two stimulus lights. Presses on the active lever result in either a 120 microL infusion of cocaine over a 4-s period via a Razel pump (Razel Scientific Instruments, Fairfax, Vt.) or delivery of a 45-mg food pellet (Bio-Serv, Frenchtown, N.J.). Presses on the inactive lever are recorded but are without consequence. Presses on the active lever result in a 20-s time-out, signaled by illumination of the stimulus light and retraction of the active lever. Once stable responding for food reinforcement is achieved at a fixed ratio (FR1: one barpress=one food pellet; 8 days, 60-min sessions), rats are shifted to a higher fixed ratio (FR5: five barpresses=one food pellet, 60-min sessions) for a period of 7 days. Following surgical recovery (5 days), food-trained rats are again allowed to lever press for food (FR5; 3 days). Rats then lever press for cocaine (0.08 mg/infusion; approximately 0.25 mg/kg/infusion) on an FR5 schedule of reinforcement for three daily sessions of 3 hr each. Following training, rats are microinjected with either 10 mM DPDPE or saline directly into the VTA prior to cocaine self-administration and active lever presses are recorded.

Results

Compared to saline, DPDPE is observed to decrease cocaine self administration in this task.

Example 14

Post Synaptic DOPR-1 and DOPR-2 are Expressed on Different Neurons in the VTA

Materials and Methods

Male rats, 20-36 days old, were anesthetized with isoflurane, and the brains were removed. Horizontal brain slices (150-250 µm thick) containing the VTA were prepared using a Vibratome (Leica Instruments, Nussloch, Germany). Slices were submerged in Ringer's solution containing (in mM): 119 NaCl, 2.5 KCl, 1.3 MgSO$_4$, 1.0 NaH$_2$PO$_4$, 2.5 CaCl$_2$, 26.2 NaHCO$_3$, and 11 glucose saturated with 95% O$_2$-5% CO$_2$ and allowed to recover at 35° C. for at least 1 hr.

Individual slices were visualized under a Zeiss Axioskop with differential interference contrast optics and infrared illumination. Whole-cell patch-clamp recordings were made at 31° C. using 2.5-4 MΩ pipettes containing (in mM): 123 K-gluconate, 10 HEPES, 0.2 EGTA, 8 NaCl, 2 MgATP, and 0.3 Na$_3$GTP, pH 7.2, osmolarity adjusted to 275). Recordings were made using an Axopatch 1-D (Axon Instruments, Union City, Calif.), filtered at 2 kHz, and collected at 5 kHz using IGOR Pro (Wavemetrics, Lake Oswego, Oreg.).

Results

| CELL # | DPDPE | DELTORPHIN |
| --- | --- | --- |
| 1 | inhibited | excited |
| 2 | inhibited | no response |
| 3 | no response | inhibited |
| 4 | excited | no response |
| 5 | no response | excited |
| 6 | inhibited | no response |

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of determining a delta opioid receptor subtype specificity of a composition, comprising:
    a) obtaining a neuronal cell preparation which comprises a cell, the cell naturally expressing at least one delta opioid receptor;
    b) exposing said preparation to a first agonist, known to selectively bind to a delta opioid subtype-1 receptor, wherein detecting a first neuronal response indicates binding of the first agonist to a delta opioid subtype-1 receptor;
    c) exposing said preparation to a second agonist, known to selectively bind to a delta opioid subtype-2 receptor, wherein detecting a first neuronal response indicates binding of the second agonist to a delta opioid subtype-2 receptor;
    d) wherein when a first neuronal response is detected and a second neuronal response is not detected, exposing a candidate composition to the cell preparation, wherein detecting a third neuronal response indicates the candidate composition is specific for delta opioid subtype-1; and
    e) wherein when a first neuronal response is not detected and a second neuronal response is detected, exposing a candidate agent to the cell preparation, wherein detecting a third neuronal response indicates the candidate composition is specific for delta opioid subtype-2.

2. The method of claim 1 wherein said first, second, or third neuronal response is detected by an electrophysiological signal.

* * * * *